US008927741B2

(12) United States Patent
Watkins et al.

(10) Patent No.: US 8,927,741 B2
(45) Date of Patent: Jan. 6, 2015

(54) SYNTHESIS OF AN ANTIVIRAL COMPOUND

(71) Applicant: Gilead Sciences, Inc., Foster City, CA (US)

(72) Inventors: William John Watkins, Saratoga, CA (US); Qi Liu, Union City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 13/801,011

(22) Filed: Mar. 13, 2013

(65) Prior Publication Data

US 2014/0051866 A1 Feb. 20, 2014

Related U.S. Application Data

(60) Provisional application No. 61/684,507, filed on Aug. 17, 2012.

(51) Int. Cl.
*C07D 409/12* (2006.01)
*C07D 333/36* (2006.01)

(52) U.S. Cl.
CPC ............ *C07D 409/12* (2013.01); *C07D 333/36* (2013.01)
USPC ............ 549/60

(58) Field of Classification Search
CPC ............ C07D 409/12
USPC ............ 549/60
See application file for complete search history.

(56) References Cited

U.S. PATENT DOCUMENTS

| | | | |
|---|---|---|---|
| 5,861,421 | A | 1/1999 | Christensen, IV et al. |
| 6,881,741 | B2 | 4/2005 | Chan Chun Kong et al. |
| 6,887,877 | B2 | 5/2005 | Chan Chun Kong et al. |
| 7,402,608 | B2 | 7/2008 | Chan Chun Kong et al. |
| 7,521,473 | B2 | 4/2009 | Lee et al. |
| 7,569,600 | B2 | 8/2009 | Denis et al. |
| 2002/0002199 | A1 | 1/2002 | Jeppesen et al. |
| 2003/0229053 | A1 | 12/2003 | Chan Chun Kong et al. |
| 2004/0116509 | A1 | 6/2004 | Chan Chun Kong et al. |
| 2005/0119332 | A1 | 6/2005 | Jeppesen et al. |
| 2006/0142347 | A1 | 6/2006 | Chan Chun Kong et al. |
| 2006/0276533 | A1 | 12/2006 | Denis et al. |
| 2007/0099929 | A1 | 5/2007 | Thede et al. |
| 2008/0299080 | A1 | 12/2008 | Chan Chun Kong et al. |
| 2009/0274655 | A1 | 11/2009 | Grimes et al. |
| 2011/0020278 | A1 | 1/2011 | Canales et al. |
| 2011/0178058 | A1 | 7/2011 | Canales et al. |
| 2011/0178129 | A1 | 7/2011 | Canales et al. |
| 2013/0052161 | A1 | 2/2013 | Watkins |

FOREIGN PATENT DOCUMENTS

| | | | |
|---|---|---|---|
| WO | 02/100846 | A1 | 12/2002 |
| WO | 02/100851 | A2 | 12/2002 |
| WO | 2004/052885 | | 6/2004 |
| WO | 2005/095386 | A1 | 10/2005 |
| WO | 2006/072347 | A2 | 7/2006 |
| WO | 2006/072348 | | 7/2006 |
| WO | 2007/093365 | A2 | 8/2007 |
| WO | 2008/058393 | A1 | 5/2008 |
| WO | 2010/065668 | | 6/2010 |
| WO | 2011/011303 | | 1/2011 |
| WO | 2011/031669 | | 3/2011 |
| WO | 2011/068715 | | 6/2011 |
| WO | WO 2011/088345 | A1 | 7/2011 |
| WO | 2012/006055 | | 1/2012 |
| WO | WO 2012/087596 | A1 | 6/2012 |

OTHER PUBLICATIONS

International Search Report from PCT/US2013/054402 issued Sep. 17, 2013 by the European Patent Office.
U.S. Appl. No. 13/800,991, filed Mar. 13, 2013, Hashash et al.
U.S. Appl. No. 13/801,039, filed Mar. 13, 2013, Evans et al.
Boyer, N, et al. (2000) "Pathogenesis, diagnosis and management of hepatitis C," *Journal of Hepatology* 32 (suppl 1):98-112.
Calisher, C. et al. (1989) "Antigenic Relationships between Flaviviruses as Determined by Cross-neutralization Tests with Polyclonal Antisera," *J. gen. Virol.* 70:37-43.
Di Bisceglie, A. et al. (1999) "Some 1.8 percent of the U.S. adult population are infected with the hepatitis C virus, most without knowing it" *Scientific American* October pp. 80-85.
Domingo, E. et al. (1985) "The quasispecies (extremely heterogeneous) nature of viral RNA genome populations: biological relevance—a review" *Gene* 40:1-8.
Dymock, B. et al. (2000) "Novel approaches to the treatment of hepatitis C virus infection," *Antiviral Chemistry & Chemotherapy* 11(2):79-96.
Fukumoto, T. et al. (1996) "Viral Dynamics of Hepatitis C Early After Orthotopic Liver Transplantation: Evidence for Rapid Turnover of Serum Virions," *Hepatology* 24:1351-1354.
Gordon, C. et al. (2005) "Control of Hepatitis C: A Medicinal Chemistry Perspective," *Journal of Medicinal Chemistry* 48(1):1-20.
Herlihy, K. et al. (2008) "Development of Intergenotypic Chimeric Replicons to Determine the Broad-Spectrum Antiviral Activities of Hepatitis C Virus Polymerase Inhibitors," *Antimicrobial Agents and Chemotherapy* 52(10):3523-3534.

(Continued)

*Primary Examiner* — Taofiq A Solola

(57) ABSTRACT

The present disclosure provides a processes for the preparation of a compound of Formula I:

(I)

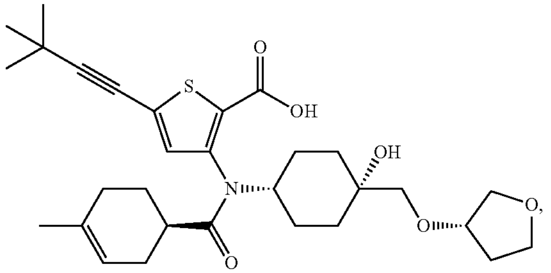

which is useful as an antiviral agent. The disclosure also provides compounds that are synthetic intermediates to compounds of Formula I.

5 Claims, No Drawings

(56) References Cited

OTHER PUBLICATIONS

Maradpour, D. et al. (2007) "Replication of Hepatitis C Virus," *Nature Reviews/ Microbiolory* 596:453-463.
Martell, M. et al. (1992) "Hepatitis C Virus (HCV) Circulates as a Population of Different but Closely Related Genomes: Quasispecies Nature of HCV Genome Distribution," *Journal of Virology* 66(5):3225-3229.
Moennig, V. et al. (1992) "The Pestiviruses," *Advances in Virus Research* 41:53-98.
Neumann, A. (1998) "Hepatitis C Viral Dynamics in Vivo and the Antiviral Efficacy of Interferon-α Therapy," *Science* 282:103-107.
Schul, W. (2007) "A Dengue Fever Viremia Model in Mice Shows Reduction in Viral Replication and Suppression of the Inflammatory Response after Treatment with Antiviral Drugs," *J. Infectious Disease* 195:665-674.
Scott, L. et al. (2002) "Interferon-α-2b Plus Ribavirin," *Drugs* 62:507-556.
International Search Report and Written Opinion for Application No. PCT/US2011/021279, mailed May 2, 2011.
International Search Report and Written Opinion for Application No. PCT/US2011/021335, mailed Feb. 22, 2011.
International Search Report and Written Opinion for Application No. PCT/US2010/042394, mailed Sep. 29, 2010.
International Search Report and Written Opinion for PCT/US2010/047983 mailed Nov. 15, 2010.
International Search Report and Written Opinion for PCT/US2012/046741 mailed Aug. 22, 2012.
Office Action for U.S. Appl. No. 12/838,684, mailed Aug. 2, 2012.
Notice of Allowance for U.S. Appl. No. 13/392,467, mailed Sep. 21, 2012.
Notice of Allowance for U.S. Appl. No. 13/006,761, mailed Oct. 3, 2012.

SYNTHESIS OF AN ANTIVIRAL COMPOUND

CROSS REFERENCE TO RELATED APPLICATIONS

This application claims the benefit under 35 U.S.C. §119 (e) to U.S. Provisional Application Ser. No. 61/684,507, filed on Aug. 17, 2012, the entirety of which is incorporated herein by reference.

BACKGROUND

The present disclosure relates generally to the field of organic synthetic methodology for the preparation of Flaviviridae virus inhibitor compounds and their synthetic intermediates.

Viruses comprising the Flaviviridae family include at least three distinguishable genera including pestiviruses, Flaviviruses, and hepaciviruses (Calisher, et al., J. Gen. Virol., 1993, 70, 37-43). While pestiviruses, such as bovine viral diarrhea virus (BVDV), classical swine fever virus (CSFV, hog cholera) and border disease virus (BDV), cause many economically important animal diseases, their importance in human disease is less well characterized (Moennig, V., et al., Adv. Vir. Res. 1992, 48, 53-98). Flaviviruses are responsible for important human diseases such as dengue fever and yellow fever while hepaciviruses cause hepatitis C virus infections in humans. Other important viral infections caused by the Flaviviridae family include West Nile virus (WNV) Japanese encephalitis virus (JEV), tick-borne encephalitis virus, Junjin virus, Murray Valley encephalitis, St Louis enchaplitis, Omsk hemorrhagic fever virus and Zika virus.

Combined, infections from the Flaviviridae virus family cause significant mortality, morbidity and economic losses throughout the world. Although compounds with anti-Flaviviridae virus activity have been disclosed, none of these are currently clinically approved antiviral therapeutics. Therefore, there remains a need to develop effective treatments for Flaviviridae virus infections. Suitable compounds for the treatment of Flaviviridae virus infections are disclosed in WO 2011/088345, including the compound of Formula I as described herein.

SUMMARY

The present disclosure provides in one embodiment a process for making a compound of Formula I:

(I)

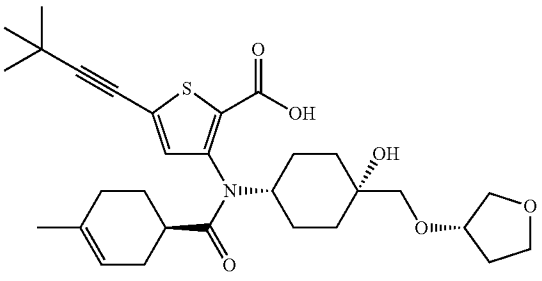

named 5-(3,3-dimethylbutyn-1-yl)-3-[(cis-4-hydroxy-4-{[(3S)-tetrahydrofuran-3-yloxy]methyl}cyclohexyl) {[(1R)-4-methylcyclohex-3-en-1-yl]carbonyl}amino]thiophene-2-carboxylic acid, or a stereoisomer, mixture of stereoisomers, pharmaceutically acceptable salt or ester thereof, comprising:

contacting a compound of Formula X, named 5-(3,3-dimethylbut-1-yn-1-yl)-3-((R)-4-methyl-N-((3S,6S)-1-oxaspiro[2.5]octan-6-yl)cyclohex-3-enecarboxamido)thiophene-2-carboxylic acid, or a stereoisomer, mixture of stereoisomers, or salt thereof, with a compound of Formula XI in the presence of a base:

(X)

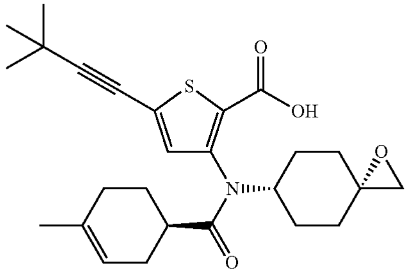

(XI)

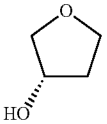

under epoxide ring opening conditions to provide the compound of Formula I or a stereoisomer, mixture of stereoisomers, pharmaceutically acceptable salt or ester thereof.

In another embodiment, the present disclosure provides a process for the preparation of a compound of Formula X:

(X)

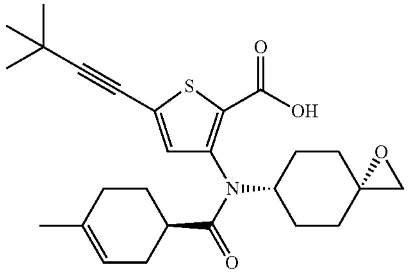

named 5-(3,3-dimethylbut-1-yn-1-yl)-3-((R)-4-methyl-N-((3S,6S)-1-oxaspiro[2.5]octan-6-yl)cyclohex-3-enecarboxamido)thiophene-2-carboxylic acid, or a stereoisomer, mixture of stereoisomers, or salt thereof, comprising:

contacting a compound of Formula VIII:

(VIII)

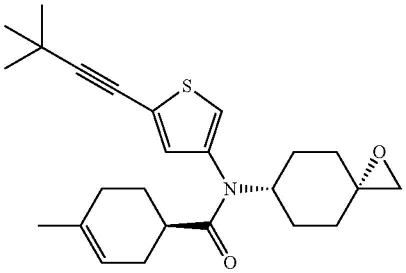

named (R)—N-(5-(3,3-dimethylbut-1-yn-1-yl)thiophen-3-yl)-4-methyl-N-((3S,6S)-1-oxaspiro[2.5]octan-6-yl)cyclohex-3-enecarboxamide, or a stereoisomer, mixture of stereoisomers, or salt thereof, with a base in the presence of $CO_2$ under carboxylation reaction conditions to provide the compound of Formula X or a stereoisomer, mixture of stereoisomers, or salt thereof.

In another embodiment, the present disclosure provides a process for the preparation of a compound of Formula VIII:

(VIII)

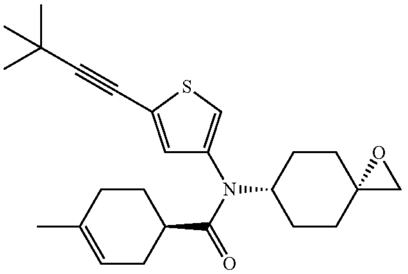

named (R)—N-(5-(3,3-dimethylbut-1-yn-1-yl)thiophen-3-yl)-4-methyl-N-((3S,6S)-1-oxaspiro[2.5]octan-6-yl)cyclohex-3-enecarboxamide, or a stereoisomer, mixture of stereoisomers, or salt thereof, comprising:

a) contacting a compound of Formula VI:

(VI)

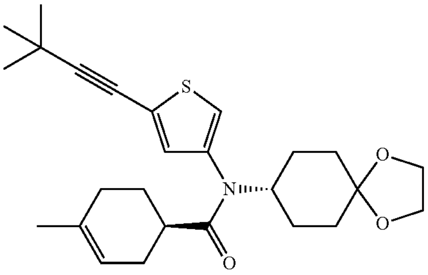

named (R)—N-(5-(3,3-dimethylbut-1-yn-1-yl)thiophen-3-yl)-4-methyl-N-(1,4-dioxaspiro[4.5]decan-8-yl)cyclohex-3-enecarboxamide, or a stereoisomer, mixture of stereoisomers, or salt thereof with an acid under ketal hydrolysis conditions to provide a compound of Formula VII:

(VII)

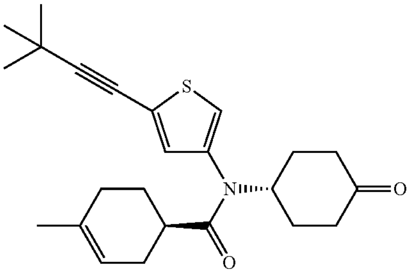

named (R)—N-(5-(3,3-dimethylbut-1-yn-1-yl)thiophen-3-yl)-4-methyl-N-(4-oxocyclohexyl)cyclohex-3-enecarboxamide, or a stereoisomer, mixture of stereoisomers, or salt thereof; and b) contacting the compound of Formula VII with trimethylsulfoxonium chloride in the presence of a base to provide the compound of Formula VIII or a stereoisomer, mixture of stereoisomers, or salt thereof.

In another embodiment, the present disclosure provides a process for the preparation of a compound of Formula VI:

(VI)

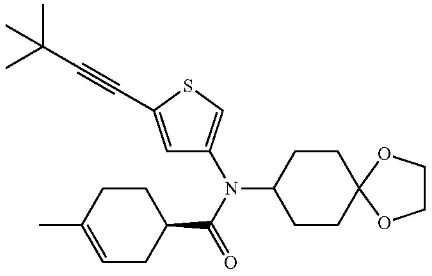

named (R)—N-(5-(3,3-dimethylbut-1-yn-1-yl)thiophen-3-yl)-4-methyl-N-(1,4-dioxaspiro[4.5]decan-8-yl)cyclohex-3-enecarboxamide, or a stereoisomer, mixture of stereoisomers, or salt thereof, comprising:

contacting a compound of Formula IV:

(IV)

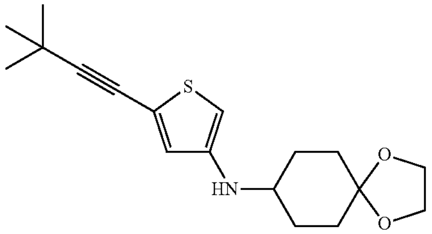

named N-(5-(3,3-dimethylbut-1-ynyl)thiophen-3-yl)-1,4-dioxaspiro[4.5]decan-8-amine, or a stereoisomer, mixture of stereoisomers, or salt thereof, with a compound of Formula V:

(V)

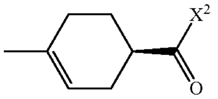

or a stereoisomer, mixture of stereoisomers, or salt thereof, under acylation reaction conditions to provide the compound of Formula VI or a stereoisomer, mixture of stereoisomers, or salt thereof; wherein $X^2$ is selected from the group consisting of: halo,

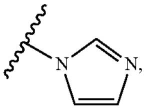
and
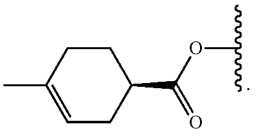

In another embodiment, the present disclosure provides a process for the preparation of a compound of Formula I:

(I)

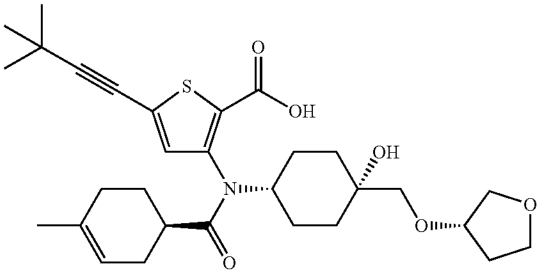

named 5-(3,3-dimethylbutyn-1-yl)-3-[(cis-4-hydroxy-4-{[(3S)-tetrahydrofuran-3-yloxy]methyl}cyclohexyl) {[(1R)-4-methylcyclohex-3-en-1-yl]carbonyl}amino]thiophene-2-carboxylic acid, or a stereoisomer, mixture of stereoisomers, pharmaceutically acceptable salt or ester thereof, comprising:

a) contacting a compound of Formula II or a stereoisomer, mixture of stereoisomers, or salt thereof, with a compound of Formula III:

(II)

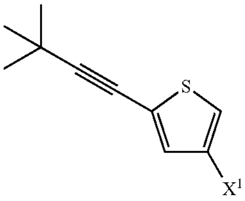

(III)

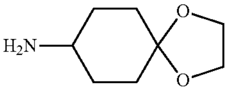

under N-arylation conditions to provide a compound of Formula IV:

(IV)

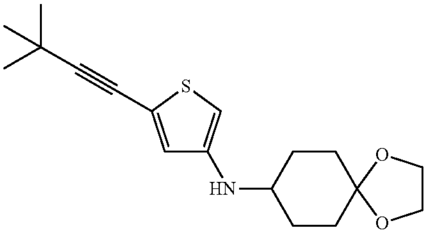

named N-(5-(3,3-dimethylbut-1-ynyl)thiophen-3-yl)-1,4-dioxaspiro[4.5]decan-8-amine or a stereoisomer, mixture of stereoisomers, or salt thereof, wherein $X^1$ is selected from the group consisting of halo, triflate, and —$B(OY)_2$, wherein each Y is independently H or $C_{1-4}$ alkyl, or two Y groups together with the atoms to which they are attached form a 5- to 6-membered ring;

b) contacting the compound of Formula IV or a stereoisomer, mixture of stereoisomers, or salt thereof with a compound of Formula V:

(V)

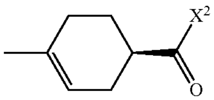

or a stereoisomer, mixture of stereoisomers, or salt thereof, under acylation reaction conditions to provide a compound of Formula VI:

(VI)

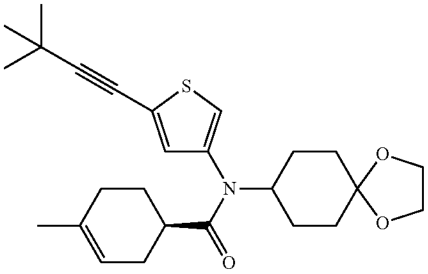

named (R)—N-(5-(3,3-dimethylbut-1-yn-1-yl)thiophen-3-yl)-4-methyl-N-(1,4-dioxaspiro[4.5]decan-8-yl)cyclohex-3-enecarboxamide, or a stereoisomer, mixture of stereoisomers, or salt thereof, wherein $X^2$ is selected from the group consisting of: halo,

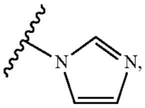

, and

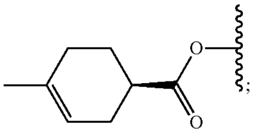

;

c) contacting the compound of Formula VI or a stereoisomer, mixture of stereoisomers, or salt thereof with an acid under ketal hydrolysis conditions to provide a compound of Formula VII:

(VII)

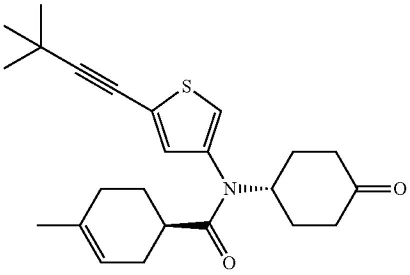

named (R)—N-(5-(3,3-dimethylbut-1-yn-1-yl)thiophen-3-yl)-4-methyl-N-(4-oxocyclohexyl)cyclohex-3-enecarboxamide, or a stereoisomer, mixture of stereoisomers, or salt thereof; and b) contacting the compound of Formula VII with trimethylsulfoxonium chloride in the presence of a base to provide the compound of Formula VIII:

(VIII)

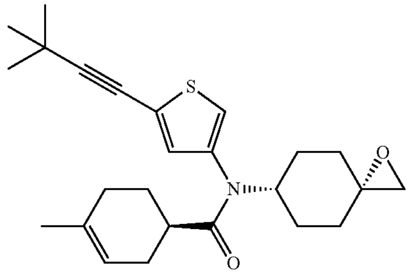

named (R)—N-(5-(3,3-dimethylbut-1-yn-1-yl)thiophen-3-yl)-4-methyl-N-((3S,6S)-1-oxaspiro[2.5]octan-6-yl)cyclohex-3-enecarboxamide or a stereoisomer, mixture of stereoisomers, or salt thereof.

d) contacting the compound of Formula VIII or a stereoisomer, mixture of stereoisomers, or salt thereof, with a base in the presence of $CO_2$ under carboxylation reaction conditions to provide a compound of Formula X:

(X)

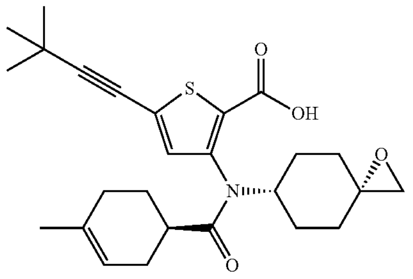

named 5-(3,3-dimethylbut-1-yn-1-yl)-3-((R)-4-methyl-N-((3S,6S)-1-oxaspiro[2.5]octan-6-yl)cyclohex-3-enecarboxamido)thiophene-2-carboxylic acid, or a stereoisomer, mixture of stereoisomers, or salt thereof; and e) contacting the compound of Formula X or a stereoisomer, mixture of stereoisomers, or salt thereof, with a compound of Formula XI:

(XI)

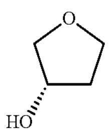

or a stereoisomer, mixture of stereoisomers, or salt thereof, in the presence of a base under epoxide ring opening conditions to provide the compound of Formula I or a stereoisomer, mixture of stereoisomers, pharmaceutically acceptable salt or ester thereof.

In another embodiment, the present disclosure provides a compound of Formula VI:

(VI)

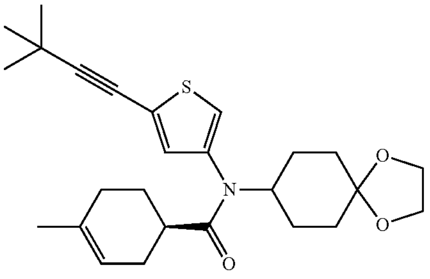

named (R)—N-(5-(3,3-dimethylbut-1-yn-1-yl)thiophen-3-yl)-4-methyl-N-(1,4-dioxaspiro[4.5]decan-8-yl)cyclohex-3-enecarboxamide, or a stereoisomer, mixture of stereoisomers, or salt thereof.

In another embodiment, the present disclosure provides a compound of Formula VII:

(VII)

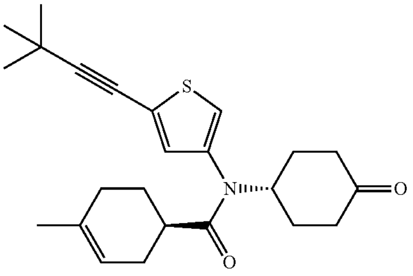

named (R)—N-(5-(3,3-dimethylbut-1-yn-1-yl)thiophen-3-yl)-4-methyl-N-(4-oxocyclohexyl)cyclohex-3-enecarboxamide, or a stereoisomer, mixture of stereoisomers, or salt thereof.

In another embodiment, the present disclosure provides a compound of Formula VIII:

(VIII)

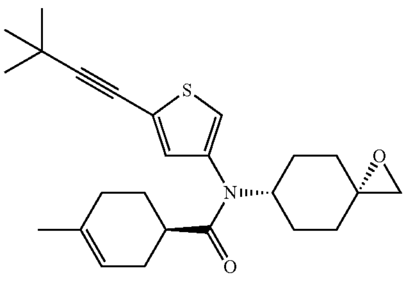

named (R)—N-(5-(3,3-dimethylbut-1-yn-1-yl)thiophen-3-yl)-4-methyl-N-((3S,6S)-1-oxaspiro[2.5]octan-6-yl)cyclohex-3-enecarboxamide, or a stereoisomer, mixture of stereoisomers, or salt thereof.

In another embodiment, the present disclosure provides a compound of Formula IX:

(IX)

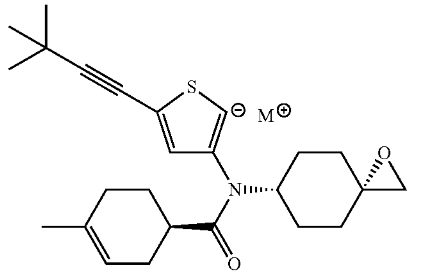

named 5-(3,3-dimethylbutyn-1-yl)-3-[(cis-4-hydroxy-4-{[(3S)-tetrahydrofuran-3-yloxy]methyl}cyclohexyl) {[(1R)-4-methylcyclohex-3-en-1-yl]carbonyl}amino]thiophene metal salt, or a stereoisomer or a mixture of stereoisomers thereof, wherein M is a metal.

More specific embodiments are described below.

DETAILED DESCRIPTION

Definitions

As used in the present specification, the following words and phrases are generally intended to have the meanings as set forth below, except to the extent that the context in which they are used indicates otherwise.

The term "alkyl" as used herein refers to a straight or branched chain, saturated hydrocarbon having the indicated number of carbon atoms. For example, ($C_1$-$C_8$)alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein throughout.

The term "substituted alkyl" refers to:

1) an alkyl group as defined above, having 1, 2, 3, 4 or 5 substituents, (in some embodiments, 1, 2 or 3 substituents) selected from the group consisting of alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —$SO_2$-alkyl, —$SO_2$-cycloalkyl, —$SO_2$-heterocyclyl, —$SO_2$-aryl and —$SO_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2; or 2) an alkyl group as defined above that is interrupted by 1-10 atoms (e.g. 1, 2, 3, 4 or 5 atoms) independently chosen from oxygen, sulfur and $NR^a$, where $R^a$ is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2, or 3) an alkyl group as defined above that has both 1, 2, 3, 4 or 5 substituents as defined above and is also interrupted by 1-10 atoms (e.g. 1, 2, 3, 4 or 5 atoms) as defined above.

The term "alkylene" refers to a diradical of a branched or unbranched saturated hydrocarbon chain, in some embodiments, having from 1 to 20 carbon atoms (e.g. 1-10 carbon atoms or 1, 2, 3, 4, 5 or 6 carbon atoms). This term is exemplified by groups such as methylene (—$CH_2$—), ethylene (—$CH_2CH_2$—), the propylene isomers (e.g., —$CH_2CH_2CH_2$— and —$CH(CH_3)CH_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkenyl" refers to a monoradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds. In some embodiments, alkenyl groups include ethenyl (or vinyl, i.e. —$CH{=}CH_2$), 1-propylene (or allyl, i.e. —$CH_2CH{=}CH_2$), isopropylene (—$C(CH_3){=}CH_2$), and the like.

The term "lower alkenyl" refers to alkenyl as defined above having from 2 to 6 carbon atoms.

The term "substituted alkenyl" refers to an alkenyl group as defined above having 1 to 5 substituents (in some embodiments, 1, 2 or 3 substituents) as defined for substituted alkyl.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—$C{\equiv}CH$), propargyl (or propynyl, i.e. —$C{\equiv}CCH_3$), and the like.

The term "substituted alkynyl" refers to an alkynyl group as defined above having 1 to 5 substituents (in some embodiments, 1, 2 or 3 substituents) as defined for substituted alkyl.

The term "hydroxy" or "hydroxyl" refers to a group —OH.

The term "alkoxy" refers to the group —O—R, where R is alkyl or —Y—Z, in which Y is alkylene and Z is alkenyl or alkynyl, where alkyl, alkenyl and alkynyl are as defined herein. In some embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group.

The term "cycloalkenyl" refers to cyclic alkyl groups of from 3 to 20 carbon atoms having a single cyclic ring or multiple condensed rings and having at least one double bond and in some embodiments, from 1 to 2 double bonds.

The terms "substituted cycloalkyl" and "substituted cycloalkenyl" refer to cycloalkyl or cycloalkenyl groups having 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —$SO_2$-alkyl, —$SO_2$-cycloalkyl, —$SO_2$-heterocyclyl, —$SO_2$-aryl and —$SO_2$-heteroaryl. The term "substituted cycloalkyl" also includes cycloalkyl groups wherein one or more of the annular carbon atoms of the cycloalkyl group has an oxo group bonded thereto. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "cycloalkoxy" refers to the group —O-cycloalkyl

The term "cycloalkenyloxy" refers to the group —O-cycloalkenyl.

The term "aryl" refers to an aromatic carbocyclic group of 6 to 20 carbon atoms having a single ring (e.g., phenyl) or multiple rings (e.g., biphenyl) or multiple condensed (fused) rings (e.g., naphthyl, fluorenyl and anthryl). In some embodiments, aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —$SO_2$-alkyl, —$SO_2$-cycloalkyl, —$SO_2$-heterocyclyl, —$SO_2$-aryl and —$SO_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "aryloxy" refers to the group —O-aryl wherein the aryl group is as defined above, and includes optionally substituted aryl groups as also defined above. The term "arylthio" refers to the group R—S—, where R is as defined for aryl.

The term "arylene" herein refers to a diradical of "aryl" as defined above that is divalent by virtue of formal removal of a hydrogen atom from the aryl.

The term "heterocyclyl," "heterocycle," or "heterocyclic" refers to a monoradical saturated group having a single ring or multiple condensed rings, having from 1 to 40 carbon atoms and from 1 to 10 hetero atoms, and from 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —$SO_2$-alkyl, —$SO_2$-cycloalkyl, —$SO_2$-heterocyclyl, —$SO_2$-aryl and —$SO_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2. Examples of heterocyclics include tetrahydrofuranyl, morpholino, piperidinyl, and the like.

The term "heterocyclooxy" refers to the group —O-heterocyclyl.

The term "heteroaryl" refers to a group comprising single or multiple rings comprising 1 to 15 carbon atoms and 1 to 4 heteroatoms selected from oxygen, nitrogen and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine. The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, 2-oxo-1,2-dihydropyridin-4-yl, and the like.

Unless otherwise constrained by the definition for the heteroaryl substituent, such heteroaryl groups can be optionally substituted with 1 to 5 substituents (in some embodiments, 1, 2 or 3 substituents) selected from the group consisting alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —$SO_2$-alkyl, —$SO_2$-cycloalkyl, —$SO_2$-heterocyclyl, —$SO_2$-aryl and —$SO_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and $—S(O)_nR^a$, in which $R^a$ is alkyl, aryl or heteroaryl and n is 0, 1 or 2. Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group —O-heteroaryl.

The term "amino" refers to the group $—NH_2$.

The term "substituted amino" refers to the group —NRR where each R is independently selected from the group consisting of hydrogen, alkyl, cycloalkyl, aryl, heteroaryl and heterocyclyl provided that both R groups are not hydrogen or a group —Y—Z, in which Y is optionally substituted alkylene and Z is alkenyl, cycloalkenyl or alkynyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and $—S(O)_nR^a$, in which $R^a$ is alkyl, aryl or heteroaryl and n is 0, 1 or 2.

The term "alkyl amine" refers to $R—NH_2$ in which R is optionally substituted alkyl.

The term "dialkyl amine" refers to R—NHR in which each R is independently an optionally substituted alkyl.

The term "trialkyl amine" refers to $NR_3$ in which each R is independently an optionally substituted alkyl.

The term "cyano" refers to the group —CN.

The term "azido" refers to a group $$—N{=}\overset{\oplus}{N}{=}\overset{\ominus}{N}.$$

The term "keto" or "oxo" refers to a group =O.

The term "carboxy" refers to a group —C(O)—OH.

The term "ester" or "carboxyester" refers to the group —C(O)OR, where R is alkyl, cycloalkyl, aryl, heteroaryl or heterocyclyl, which may be optionally further substituted by alkyl, alkoxy, halogen, $CF_3$, amino, substituted amino, cyano or $—S(O)_nR^a$, in which $R^a$ is alkyl, aryl or heteroaryl and n is 0, 1 or 2.

The term "acyl" denotes a group —C(O)R, in which R is hydrogen, optionally substituted alkyl, optionally substituted cycloalkyl, optionally substituted cycloalkenyl, optionally substituted heterocyclyl, optionally substituted aryl or optionally substituted heteroaryl.

The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and $—S(O)_nR^a$, in which $R^a$ is alkyl, aryl or heteroaryl and n is 0, 1 or 2.

The term "aminocarbonyl" refers to the group —C(O)NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and $—S(O)_nR^a$, in which $R^a$ is alkyl, aryl or heteroaryl and n is 0, 1 or 2.

The term "acyloxy" refers to the groups —OC(O)-alkyl, —OC(O)-cycloalkyl, —OC(O)-aryl, —OC(O)-heteroaryl and —OC(O)-heterocyclyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and $—S(O)_nR^a$, in which $R^a$ is alkyl, aryl or heteroaryl and n is 0, 1 or 2.

The term "acylamino" refers to the group —NRC(O)R where each R is independently hydrogen, alkyl, cycloalkyl, aryl, heteroaryl or heterocyclyl. All substituents may be optionally further substituted by alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and $—S(O)_nR^a$, in which $R^a$ is alkyl, aryl or heteroaryl and n is 0, 1 or 2.

The term "alkoxycarbonylamino" refers to a group $—N(R^c)C(O)OR$ in which R is optionally substituted alkyl and $R^c$ is hydrogen or optionally substituted alkyl.

The term "aminocarbonylamino" refers to the group $—NR^dC(O)NRR$, wherein $R^d$ is hydrogen or optionally substituted alkyl and each R is independently selected from the group consisting of hydrogen, alkyl, cycloalkyl, aryl, heteroaryl and heterocyclyl. Unless otherwise constrained by the definition, all substituents may optionally be further substituted by 1, 2 or 3 substituents selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, $—SO_2$-alkyl, $—SO_2$-cycloalkyl, $—SO_2$-heterocyclyl, $—SO_2$-aryl and $—SO_2$-heteroaryl.

The term "thiol" refers to the group —SH.

The term "thiocarbonyl" refers to a group =S.

The term "alkylthio" refers to the group —S-alkyl.

The term "substituted alkylthio" refers to the group —S-substituted alkyl.

The term "heterocyclylthio" refers to the group —S-heterocyclyl.

The term "arylthio" refers to the group —S-aryl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, cycloalkyl, heterocyclyl, aryl or heteroaryl. "Substituted sulfoxide" refers to a group —S(O)R, in which R is substituted alkyl, substituted cycloalkyl, substituted heterocyclyl, substituted aryl or substituted heteroaryl, as defined herein.

The term "sulfone" refers to a group —$S(O)_2R$, in which R is alkyl, cycloalkyl, heterocyclyl, aryl or heteroaryl. "Substituted sulfone" refers to a group —$S(O)_2R$, in which R is substituted alkyl, substituted cycloalkyl, substituted heterocyclyl, substituted aryl or substituted heteroaryl, as defined herein.

The term "aminosulfonyl" refers to the group —$S(O)_2$ NRR, wherein each R is independently selected from the group consisting of hydrogen, alkyl, cycloalkyl, aryl, heteroaryl and heterocyclyl. Unless otherwise constrained by the definition, all substituents may optionally be further substituted by 1, 2 or 3 substituents selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —$SO_2$-alkyl, —$SO_2$-cycloalkyl, —$SO_2$-heterocyclyl, —$SO_2$-aryl and —$SO_2$-heteroaryl.

The term "hydroxyamino" refers to the group —NHOH.

The term "alkoxyamino" refers to the group —NHOR in which R is optionally substituted alkyl.

The term "halogen" or "halo" refers to fluoro, bromo, chloro and iodo.

The term "triflate" refers to the trifluoromethanesulfonate group (–$OSO_2$—$CF_3$).

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "alkyl-substituted phenyl", where the attachment sites are not explicit, may have any available site of the alkyl group attached to any available site of the phenyl group. In this regard, an "available site" is a site of the group at which a hydrogen of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

A compound of a given Formula (e.g. the compound of Formula I) is intended to encompass the compounds of the disclosure, and the salts (e.g. pharmaceutically acceptable salts), esters, isomers, tautomers, solvates, isotopes, hydrates, co-crystals, co-formers and/or prodrugs of such compounds. Additionally, the compounds of the disclosure may possess one or more asymmetric centers, and can be produced as a racemic mixture or as individual enantiomers or diastereoisomers. The number of stereoisomers present in any given compound of a given Formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that contain stereogenic atoms which contain the same connectivity, but which differ only in the way the atoms are arranged in space. The term "stereoisomers" as used herein includes both "enantiomers" and "diastereomers."

"Enantiomers" are a pair of stereoisomers that are non-superimposable mirror images of each other and do not contain a plane of symmetry. A 1:1 mixture of a pair of enantiomers is a "racemic" mixture. The term "(±)" is used to designate a racemic mixture where appropriate.

"Diastereoisomers" are stereoisomers that have at least two stereogenic atoms and may contain a plane of symmetry, but which are not mirror-images of each other in the absence of a plane of symmetry.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

If there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of it.

The term "solvate" refers to a complex formed by the combining of a compound of Formula I, or any other Formula as disclosed herein, and a solvent. As used herein, the term "solvate" includes a hydrate (i.e., a solvate when the solvent is water).

The term "hydrate" refers to the complex formed by the combining of a compound of Formula I, or any Formula disclosed herein, and water.

The term "co-crystal" refers to a crystalline material formed by combining a compound of Formula I, or any Formula disclosed herein and one or more co-crystal formers (i.e., a molecule, ion or atom). In certain instances, co-crystals may have improved properties as compared to the parent form (i.e., the free molecule, zwitter ion, etc.) or a salt of the parent compound. Improved properties can be increased solubility, increased dissolution, increased bioavailability, increased dose response, decreased hygroscopicity, a crystalline form of a normally amorphous compound, a crystalline form of a difficult to salt or unsaltable compound, decreased form diversity, more desired morphology, and the like. Methods for making and characterizing co-crystals are known to those of skill in the art.

The terms "co-former" or "co-crystal former" refer to the non-ionic association of a compound of Formula I, or any Formula disclosed herein with one or more molecules, ions or atoms. Exemplary co-formers are inorganic or organic bases and/or acids.

Any formula or structure given herein, including Formula I, or any Formula disclosed herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorus, fluorine and chlorine, such as but not limited to $^{2}H$ (deuterium, D), $^{3}H$ (tritium) $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^{3}H$, $^{13}C$ and $^{14}C$ are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also included compounds of Formula I, or any Formula disclosed herein, in which from 1 to "n" hydrogens attached to a carbon atom is/are replaced by deuterium, in which n is the number of hydrogens in the molecule. Such compounds exhibit increased resistance to metabolism and are thus useful for increasing the half life of any compound of Formula I when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogen atoms have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life or reduced dosage requirements. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the Formula I, or any Formula disclosed herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. See: P. Heinrich Stahl and Camille G. Wermuth (Eds.) Pharmaceutical Salts Properties, Selection, and Use (International Union of Pure and Applied Chemistry), Wiley-VCH; 2nd Revised Edition (May 16, 2011). Pharmaceutically acceptable base addition salts can be prepared from inorganic and organic bases.

Pharmaceutically acceptable base addition salts may be salts prepared from inorganic and organic bases and pharmaceutically acceptable acid addition salts may be salts prepared from inorganic and organic acids.

Salts of the compounds disclosed herein can be base addition salts or acid addition salts depending on the reactivity of the functional groups present on the specific compound. Base addition salts can be derived from inorganic or organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure)N($R^{30}$)($R^{31}$)($R^{32}$), wherein mono-substituted amines have 2 of the three substituents on nitrogen ($R^{30}$, $R^{31}$ and $R^{32}$) as hydrogen, di-substituted amines have 1 of the three substituents on nitrogen ($R^{30}$, $R^{31}$ and $R^{32}$) as hydrogen, whereas tri-substituted amines have none of the three substituents on nitrogen ($R^{30}$, $R^{31}$ and $R^{32}$) as hydrogen. $R^{30}$, $R^{31}$ and $R^{32}$ are selected from a variety of substituents such as hydrogen, optionally substituted alkyl, aryl, heteroayl, cycloalkyl, cycloalkenyl, heterocyclyl and the like. The above-mentioned amines refer to the compounds wherein either one, two or three substituents on the nitrogen are as listed in the name. For example, the term "cycloalkenyl amine" refers to cycloalkenyl-$NH_2$, wherein "cycloalkenyl" is as defined herein. The term "diheteroarylamine" refers to NH(heteroaryl)$_2$, wherein "heteroaryl" is as defined herein and so on.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Acid addition salts can be derived from inorganic or organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Any of the salts disclosed herein may be optionally pharmaceutically acceptable.

The term "acylation reaction conditions" refers to the reaction conditions under which an acyl moiety is installed onto a suitable substrate, where the term "acyl" is as defined herein. "Acylation reaction conditions" typically comprise an acylating agent, such as an acyl halide, and a suitable base, such as an amine base (e.g., N,N-diisopropylethylamine, or 2,2,6,6-tetramethylpiperidine).

The term "N-arylation reaction conditions" refers to the reaction conditions under which an amine moiety is installed onto a suitable aromatic substrate, where the term "amine" is as defined herein. The "N-arylation reaction conditions" as disclosed herein typically comprise a catalyst, such as a palladium, platinum, or copper based catalyst, in the presence of a ligand, such as 5-(di-tert-butylphosphino)-1',3',5'-triphenyl-1'H-[1,4']bipyrazole, 2-(di-tert-butyl-phosphino)-1-phenyl-1H-pyrrole, 2-(di-tert-butylphosphino)-1-(2-methoxyphenyl)-1H-pyrrole, acetylacetone, acetylcyclohexanone, isobutyrylcyclohexanone, $N^1,N^2$-dimethylcyclohexane-1,2-diamine, L-proline, BINAP, or N,N-diethylsalicylamide.

The term "carboxylation reaction conditions" refers to the reaction conditions under which a carboxyl moiety is installed onto a suitable substrate, where the term "carboxyl" is as defined herein. "Carboxylation reaction conditions" typically comprise a base, which base is capable of deprotonating a carbon atom of the substrate (e.g., sodium hydride, potassium hydride, sodium hexamethyldisilazine, n-butyl lithium, n-hexyl lithium, phenyl lithium, ethyl lithium, lithium tetramethylpiperidide, or lithium diisopropylamide) and carbon dioxide.

In addition, abbreviations as used herein have respective meanings as follows:

| | |
|---|---|
| BINAP | 2,2'-bis(diphenylphosphino)-1,1'-binaphthyl |
| br. s | broad singlet |
| DCE | dichloroethane |
| DCM | dichloromethane |
| dd | doublet of doublets |
| DMF | dimethylformamide |
| DMSO | dimethylsulfoxide |
| dr | diastereomeric ratio |
| ee | enantiomeric excess |
| equiv | equivalents |
| $Et_3N$ or TEA | triethylamine |
| EtOAc | ethyl acetate |
| EtOH | ethanol |
| GC | gas chromatography |
| h | hour(s) |

-continued

| | |
|---|---|
| HPLC | high pressure liquid chromatography |
| Hz | hertz |
| Kg | kilogram |
| KOtBu | potassium tert-butoxide |
| L | liter |
| LDA | lithium diisopropylamide |
| m | multiplet |
| $MeNH_2$ | methylamine |
| MHz | megahertz |
| mmol | millimole |
| MS | mass spectroscopy |
| NLT | no less than |
| NMP | N-methylpyrrolidone |
| NMR | nuclear magnetic resonance |
| s | singlet |
| THF | tetrahydrofuran |

Processes

As described generally above, the disclosure provides in some embodiments processes for making a compound of Formula I. In another embodiment, the disclosure provides a processes for making intermediates for the compound of Formula I.

In one embodiment, the disclosure provides a process for the preparation of a compound of Formula I:

(I)

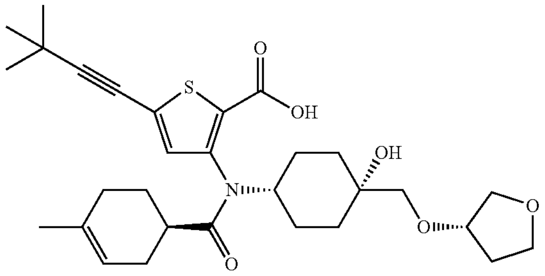

named 5-(3,3-dimethylbutyn-1-yl)-3-[(cis-4-hydroxy-4-{[(3S)-tetrahydrofuran-3-yloxy]methyl}cyclohexyl) {[(1R)-4-methylcyclohex-3-en-1-yl]carbonyl}amino]thiophene-2-carboxylic acid, or a stereoisomer, mixture of stereoisomers, pharmaceutically acceptable salt or ester thereof, comprising:

a) contacting a compound of Formula II or a stereoisomer, mixture of stereoisomers, or salt thereof, with a compound of Formula III:

(II)

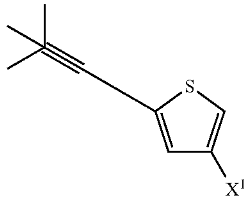

(III)

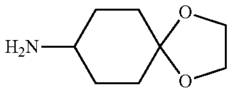

under N-arylation conditions to provide a compound of Formula IV:

(IV)

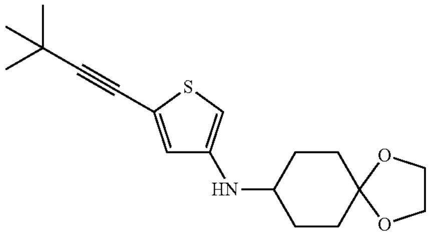

named N-(5-(3,3-dimethylbut-1-ynyl)thiophen-3-yl)-1,4-dioxaspiro[4.5]decan-8-amine, or a stereoisomer, mixture of stereoisomers, or salt thereof, wherein $X^1$ is selected from the group consisting of halo, triflate, and —$B(OY)_2$, wherein each Y is independently H or $C_{1-4}$ alkyl, or two Y groups together with the atoms to which they are attached form a 5- to 6-membered ring;

b) contacting the compound of Formula IV or a stereoisomer, mixture of stereoisomers, or salt thereof with a compound of Formula V:

(V)

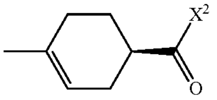

or a stereoisomer, mixture of stereoisomers, or salt thereof, under acylation reaction conditions to provide a compound of Formula VI:

(VI)

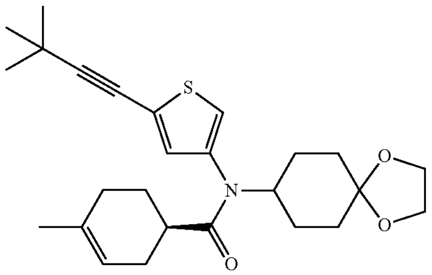

named (R)—N-(5-(3,3-dimethylbut-1-yn-1-yl)thiophen-3-yl)-4-methyl-N-(1,4-dioxaspiro[4.5]decan-8-yl)cyclohex-3-enecarboxamide, or a stereoisomer, mixture of stereoisomers, or salt thereof, wherein $X^2$ is selected from the group consisting of: halo,

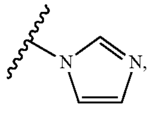

and

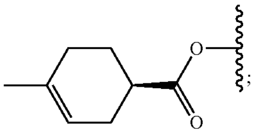

;

c) contacting the compound of Formula VI or a stereoisomer, mixture of stereoisomers, or salt thereof with an acid under ketal hydrolysis conditions to provide a compound of Formula VII:

(VII)

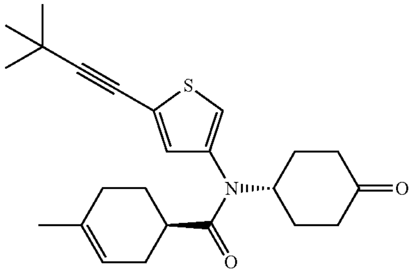

named (R)—N-(5-(3,3-dimethylbut-1-yn-1-yl)thiophen-3-yl)-4-methyl-N-(4-oxocyclohexyl)cyclohex-3-enecarboxamide, or a stereoisomer, mixture of stereoisomers, or salt thereof;

d) contacting the compound of Formula VII with trimethylsulfoxonium chloride in the presence of a base to provide the compound of Formula VIII:

(VIII)

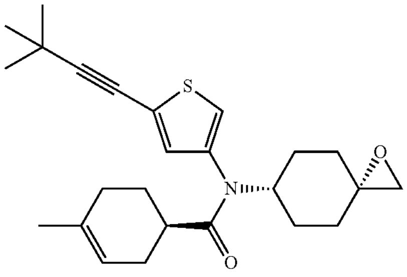

named (R)—N-(5-(3,3-dimethylbut-1-yn-1-yl)thiophen-3-yl)-4-methyl-N-((3S,6S)-1-oxaspiro[2.5]octan-6-yl)cyclohex-3-enecarboxamide or a stereoisomer, mixture of stereoisomers, or salt thereof;

e) contacting the compound of Formula VIII or a stereoisomer, mixture of stereoisomers, or salt thereof, with a base in the presence of $CO_2$ under carboxylation reaction conditions to provide a compound of Formula X:

(X)

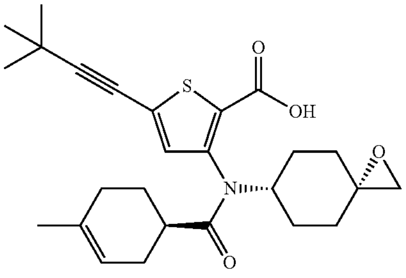

named 5-(3,3-dimethylbut-1-yn-1-yl)-3-((R)-4-methyl-N-((3S,6S)-1-oxaspiro[2.5]octan-6-yl)cyclohex-3-enecarboxamido)thiophene-2-carboxylic acid, or a stereoisomer, mixture of stereoisomers, or salt thereof; and f) contacting the compound of Formula X or a stereoisomer, mixture of stereoisomers, or salt thereof, with a compound of Formula XI:

(XI)

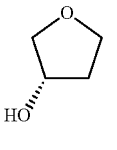

or a stereoisomer, mixture of stereoisomers, or salt thereof, in the presence of a base under epoxide ring opening conditions to provide the compound of Formula I or a stereoisomer, mixture of stereoisomers, pharmaceutically acceptable salt or ester thereof.

A variety of acylating agents (e.g., carbodiimides, N-methylimidazoles, and the like) and/or other derivatives of Formula XI (e.g., activated esters, mixed anhydrides, acyltriazines, activated phosphates, organophosphorus esters, the like) are suitable for use in the acylation reaction of step b). In certain embodiments this disclosure provides a compound of Formula V, wherein $X^2$ is halo. In certain embodiments, $X^2$ is bromo.

A variety of other N-arylating agents are also suitable for use in step a). Non-limiting examples include cyclic organoboron compounds such as cyclic trimeric anhydrides (boroxines), cyclic boronic esters (boronates), and the like. In certain embodiments, this disclosure provides a compound of Formula II, wherein $X^1$ is halo. In certain embodiments, $X^1$ is chloro.

In one embodiment, the disclosure provides a process for the preparation of a compound of Formula I:

(I)

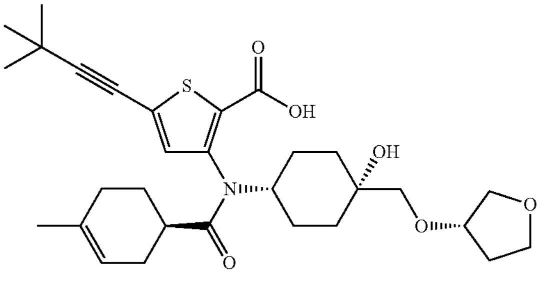

named 5-(3,3-dimethylbutyn-1-yl)-3-[(cis-4-hydroxy-4-{[(3S)-tetrahydrofuran-3-yloxy]methyl}cyclohexyl) {[(1R)-4-methylcyclohex-3-en-1-yl]carbonyl}amino]thiophene-2-carboxylic acid, or a stereoisomer, mixture of stereoisomers, pharmaceutically acceptable salt or ester thereof, comprising:

contacting a compound of Formula X, named 5-(3,3-dimethylbut-1-yn-1-yl)-3-((R)-4-methyl-N-((3S,6S)-1-oxaspiro[2.5]octan-6-yl)cyclohex-3-enecarboxamido)thiophene-2-carboxylic acid, or a stereoisomer, mixture of stereoisomers, or salt thereof with a compound of Formula XI in the presence of a base:

(X)

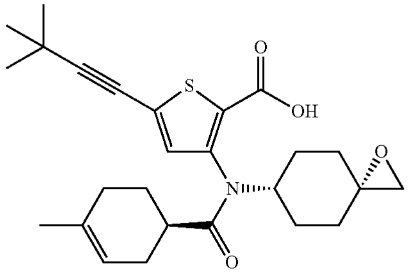

(XI)

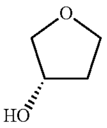

under epoxide ring opening conditions to provide the compound of Formula I or a stereoisomer, mixture of stereoisomers, pharmaceutically acceptable salt or ester thereof.

In another embodiment, the disclosure provides a process for the preparation of a compound of Formula X:

(X)

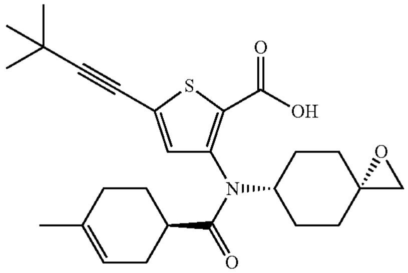

named 5-(3,3-dimethylbut-1-yn-1-yl)-3-((R)-4-methyl-N-((3S,6S)-1-oxaspiro[2.5]octan-6-yl)cyclohex-3-enecarboxamido)thiophene-2-carboxylic acid, or a stereoisomer, mixture of stereoisomers, or salt thereof; comprising:

contacting a compound of Formula VIII, named (R)—N-(5-(3,3-dimethylbut-1-yn-1-yl)thiophen-3-yl)-4-methyl-N-((3S,6S)-1-oxaspiro[2.5]octan-6-yl)cyclohex-3-enecarboxamide, or a stereoisomer, mixture of stereoisomers, or salt thereof, with a base in the presence of $CO_2$:

(VIII)

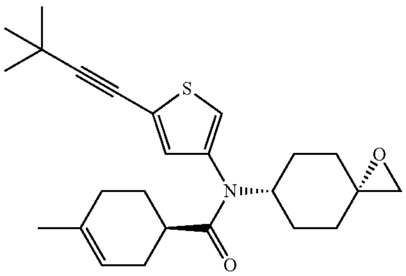

under carboxylation reaction conditions to provide the compound of Formula X or a stereoisomer, mixture of stereoisomers, or salt thereof.

In one embodiment, the carboxylation reaction conditions comprise about a three-fold equivalent of the base. A variety of bases are suitable for use, provided that the base is capable of deprotecting the thiophene at the 5-position. Non-limiting examples of suitable bases include sodium hydride, potassium hydride, sodium hexamethyldisilazine, n-butyl lithium, n-hexyl lithium, phenyl lithium, ethyl lithium, lithium tetramethylpiperidide, and lithium diisopropylamide.

In certain embodiments, the carboxylation reaction conditions comprise a temperature from about −78° C. to about 45° C. In other embodiments, the carboxylation reaction temperature is from about −20° C. to about 20° C.

In another embodiment, the disclosure provides a process for the preparation of a compound of Formula VIII:

(VIII)

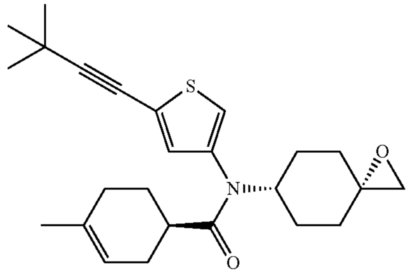

named (R)—N-(5-(3,3-dimethylbut-1-yn-1-yl)thiophen-3-yl)-4-methyl-N-((3S,6S)-1-oxaspiro[2.5]octan-6-yl)cyclohex-3-enecarboxamide, or a stereoisomer, mixture of stereoisomers, or salt thereof, or a stereoisomer, mixture of stereoisomers, or salt thereof, comprising:

a) contacting a compound of Formula VI:

(VI)

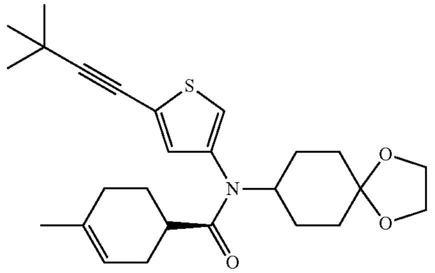

named (R)—N-(5-(3,3-dimethylbut-1-yn-1-yl)thiophen-3-yl)-4-methyl-N-(1,4-dioxaspiro[4.5]decan-8-yl)cyclohex-3-enecarboxamide, or a stereoisomer, mixture of stereoisomers, or salt thereof with an acid under ketal hydrolysis conditions to provide a compound of Formula VII:

(VII)

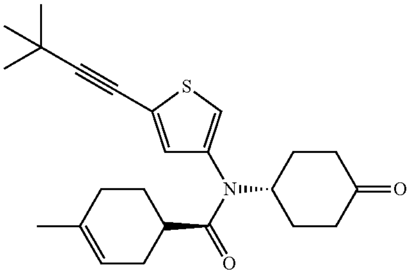

named (R)—N-(5-(3,3-dimethylbut-1-yn-1-yl)thiophen-3-yl)-4-methyl-N-(4-oxocyclohexyl)cyclohex-3-enecarboxamide, or a stereoisomer, mixture of stereoisomers, or salt thereof; and b) contacting the compound of Formula VII with trimethylsulfoxonium chloride in the presence of a base to provide the compound of Formula VIII or a stereoisomer, mixture of stereoisomers, or salt thereof.

In another embodiment, the disclosure provides a process for the preparation of a compound of Formula VI:

(VI)

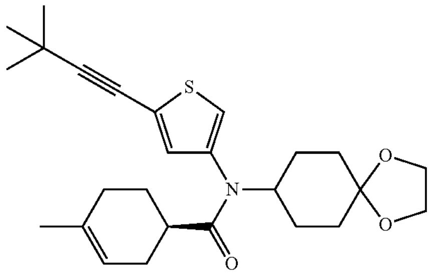

named (R)—N-(5-(3,3-dimethylbut-1-yn-1-yl)thiophen-3-yl)-4-methyl-N-(1,4-dioxaspiro[4.5]decan-8-yl)cyclohex-3-enecarboxamide, or a stereoisomer, mixture of stereoisomers, or salt thereof, comprising:

contacting a compound of Formula IV:

(IV)

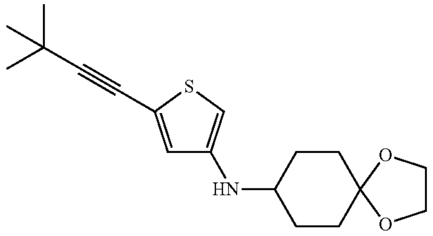

IV named N-(5-(3,3-dimethylbut-1-ynyl)thiophen-3-yl)-1,4-dioxaspiro[4.5]decan-8-amine or a stereoisomer, mixture of stereoisomers, or salt thereof, with a compound of Formula V:

(V)

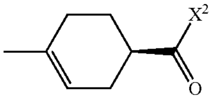

or a stereoisomer, mixture of stereoisomers, or salt thereof, under acylation reaction conditions to provide the compound of Formula VI or a stereoisomer, mixture of stereoisomers, or salt thereof, wherein $X^2$ is selected from the group consisting of: halo,

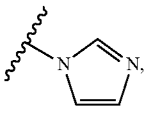

and

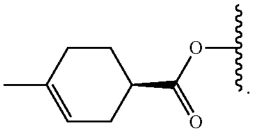

In one embodiment, the acylation reaction conditions comprise a base. Suitable bases include substituted or unsubstituted tertiary amines, which includes amines where the three substituents, together with the amino nitrogen, form a heteroaryl group. In a further embodiment, the base is imidazole, pyridine, N,N-diisopropylethylamine or 2,2,6,6-tetramethylpiperidine.

In another embodiment, the acylation reaction conditions of the disclosure comprise a temperature from about −45° C. to about 100° C. In another embodiment, the acylation reaction conditions comprise a temperature from about 0° C. to about 20° C.

In another embodiment, the disclosure provides a process for the compound of Formula IV:

(IV)

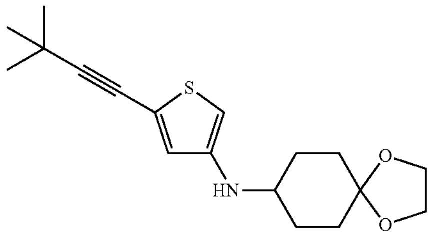

IV named N-(5-(3,3-dimethylbut-1-ynyl)thiophen-3-yl)-1,4-dioxaspiro[4.5]decan-8-amine or a stereoisomer, mixture of stereoisomers, or salt thereof, comprising contacting a compound of Formula II or a stereoisomer, mixture of stereoisomers, or salt thereof, with a compound of Formula III:

(II)

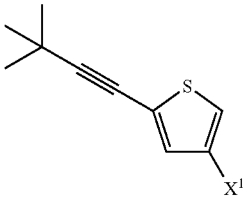

-continued (III)

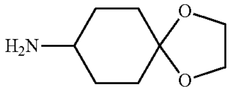

under N-arylation conditions to provide the compound of Formula IV, wherein $X^1$ is selected from the group consisting of halo, triflate, and —$B(OY)_2$, wherein each Y is independently H or $C_{1-4}$ alkyl, or two Y groups together with the atoms to which they are attached form a 5- to 6-membered ring.

In one embodiment, the N-arylation reaction conditions of the disclosure comprise a catalyst. In a further embodiment, the catalyst is a palladium, platinum, or copper based catalyst. In another embodiment, the catalyst is selected from the group consisting of copper(I) chloride, tris(dibenzylideneacetone)dipalladium(0), copper(II) chloride, copper(I) bromide, copper(II) bromide, copper(I) acetate, copper(II) acetate, copper(II) acetylacetonate, copper(I) trifluoromethanesulfonate, copper(II) trifluoromethanesulfonate, copper(I) thiophene-2-carboxylate, copper(I) iodide, and the like.

In another embodiment, the N-arylation reaction conditions of the disclosure further comprise a ligand. In a further embodiment, the ligand is selected from the group consisting of 5-(di-tert-butylphosphino)-1',3',5'-triphenyl-1'H-[1,4']bi-pyrazole, 2-(di-tert-butyl-phosphino)-1-phenyl-1H-pyrrole, 2-(di-tert-butylphosphino)-1-(2-methoxyphenyl)-1H-pyrrole, acetylacetone, acetylcyclohexanone, isobutyrylcyclohexanone, $N^1$,$N^2$-dimethylcyclohexane-1,2-diamine, L-proline, BINAP, N,N-diethylsalicylamide, and the like.

In another embodiment, the N-arylation reaction conditions of the disclosure further comprise a base. Exemplary bases include metal hydroxides, carbonates, alkoxides, and the like. In certain embodiments, the base is selected from the group consisting of potassium hydroxide, sodium hydroxide, sodium tert-amylate, cesium carbonate, cesium hydroxide, potassium phosphate tribasic, sodium tertbutoxide, sodium methoxide, and sodium ethoxide.

The intermediates in the process for the synthesis of Formula I can be used in the next step with or without purification. The conventional means of purification include recrystallization, chromatography (e.g. adsorbant, ion exchange, and HPLC), and the like.

In some embodiments, the means of purification can include chiral resolution in order to increase the enantiomeric purity of one or more intermediates in the process for the synthesis of Formula I and/or Formula I. Such methods can include for example, crystallization, a chiral resolving agent, and/or chiral chromatography. For example, in some embodiments, compounds of Formula I can be further purified via crystallization with cinonine alkaloids.

Compounds

In other embodiments, the disclosure provides for intermediate compounds that are useful in the processes described herein. Thus, for instance, one embodiment is a compound of Formula VI:

(VI)

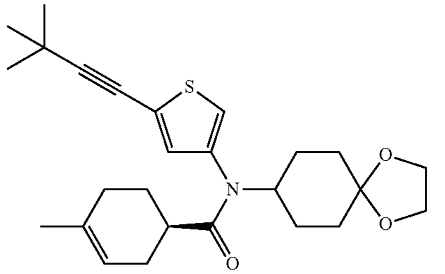

named (R)—N-(5-(3,3-dimethylbut-1-yn-1-yl)thiophen-3-yl)-4-methyl-N-(1,4-dioxaspiro[4.5]decan-8-yl)cyclohex-3-enecarboxamide, or a stereoisomer, mixture of stereoisomers, or salt thereof.

Another embodiment is a compound of Formula VII:

(VII)

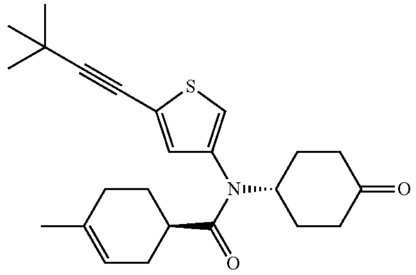

named (R)—N-(5-(3,3-dimethylbut-1-yn-1-yl)thiophen-3-yl)-4-methyl-N-(4-oxocyclohexyl)cyclohex-3-enecarboxamide, or a stereoisomer, mixture of stereoisomers, or salt thereof.

Another embodiment is a compound of Formula VIII:

(VIII)

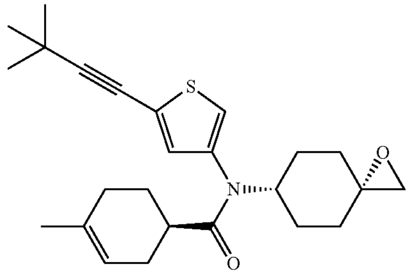

named (R)—N-(5-(3,3-dimethylbut-1-yn-1-yl)thiophen-3-yl)-4-methyl-N-((3S,6S)-1-oxaspiro[2.5]octan-6-yl)cyclohex-3-enecarboxamide or a stereoisomer, mixture of stereoisomers, or salt thereof.

Another embodiment is a compound of Formula IX:

(IX)

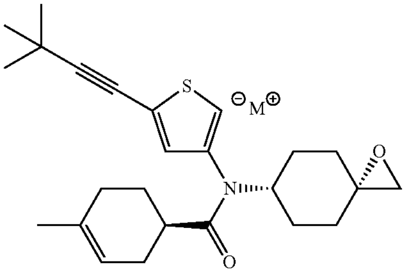

named 5-(3,3-dimethylbutyn-1-yl)-3-[(cis-4-hydroxy-4-{[(3S)-tetrahydrofuran-3-yloxy]methyl}cyclohexyl) {[(1R)-4-methylcyclohex-3-en-1-yl]carbonyl}amino]thiophene metal salt, or a stereoisomer or a mixture of stereoisomers thereof, wherein M is a metal.

In some embodiments, the metal is lithium, potassium, sodium, and the like. In certain embodiments, the metal is lithium.

Co-formers and/or co-crystals of any one of the Formulas disclosed herein are also provided.

The present disclosure is not to be limited in scope by the specific embodiments disclosed in the examples, which are intended to be illustrations of a few embodiments of the disclosure, nor is the disclosure to be limited by any embodiments that are functionally equivalent within the scope of this disclosure. Indeed, various modifications of the disclosure in addition to those shown and described herein will become apparent to those skilled in the art and are intended to fall within the scope of the appended claims. To this end, it should be noted that one or more hydrogen atoms or methyl groups can be omitted from the drawn structures consistent with accepted shorthand notation of such organic compounds, and that one skilled in the art of organic chemistry would readily appreciate their presence.

EXAMPLES

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of compounds described herein, may be accomplished as described in the following examples. If available, reagents may be purchased commercially, e.g. from Sigma Aldrich or other chemical suppliers. Unless otherwise noted, the starting materials for the following reactions may be obtained from commercial sources.

Example 1
Synthesis of 5-(3,3-dimethylbutyn-1-yl)-3-[(cis-4-hydroxy-4-{[(3S)-tetrahydrofuran-3-yloxy]methyl}cyclohexyl) {[(1R)-4-methylcyclohex-3-en-1-yl]carbonyl}amino]thiophene-2-carboxylic acid (I)
Compound of Formula I was synthesized as shown below:
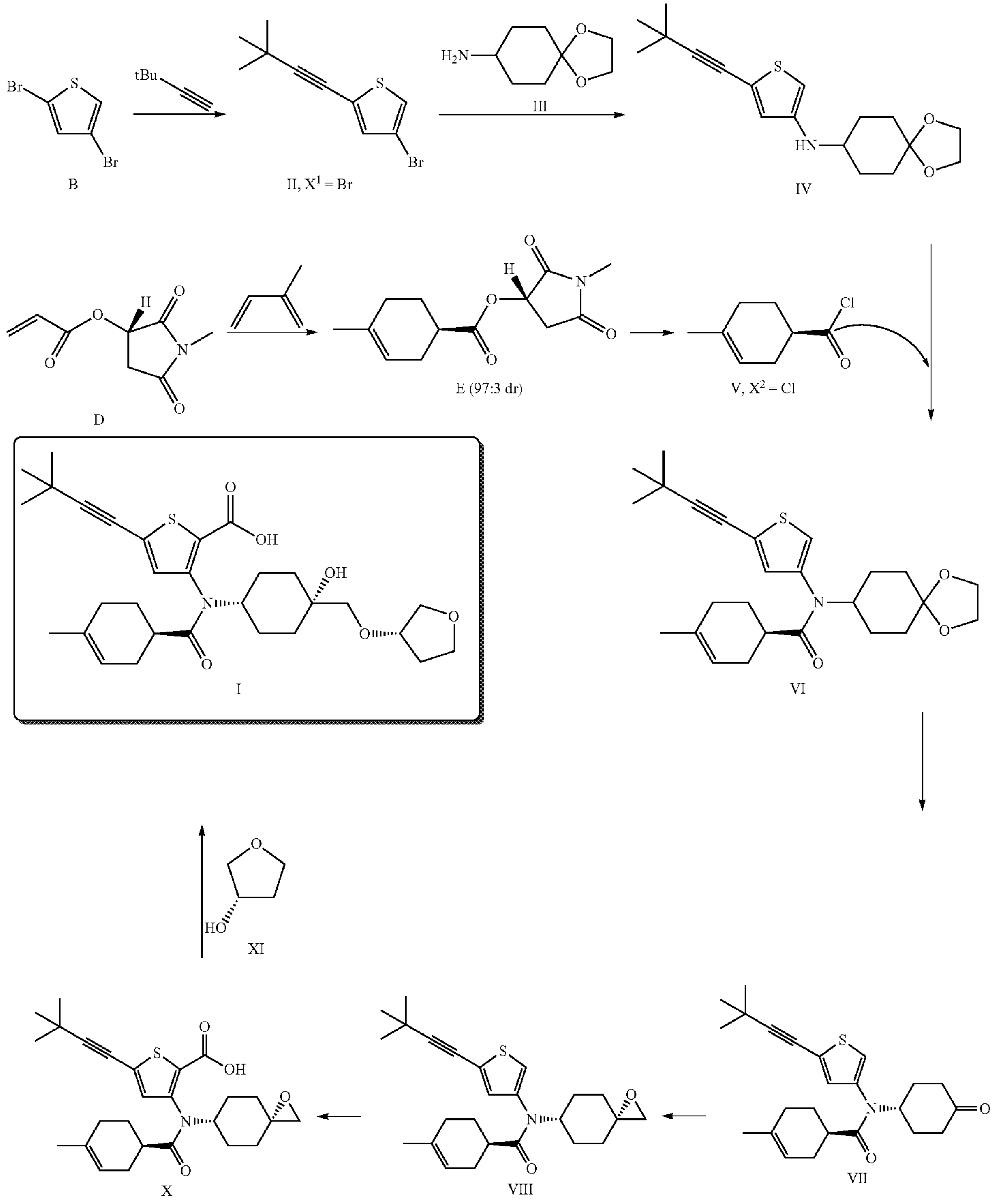

Step 1: Synthesis of 4-bromo-2-(3,3-dimethylbut-1-ynyl)thiophene II ($X^1$=Br)

A. Bromination, De-Bromination, and Alkynylation to Provide Intermediate II ($X^1$=Br):

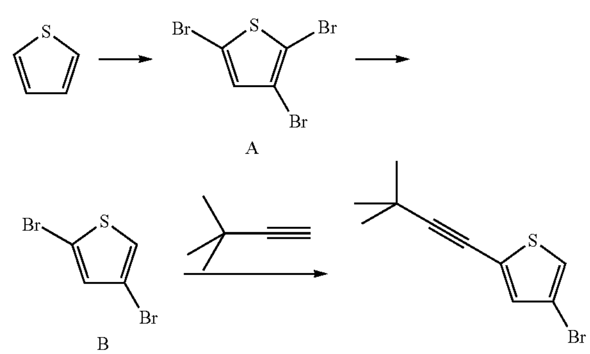

A

B

II ($X^1$ = Br)

i. Bromination to Prepare Intermediate A:

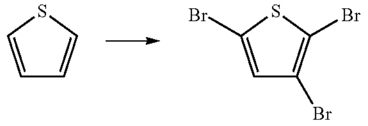

A

Thiophene was brominated to provide 2,3,5-tribromothiophene A according to the following procedure. A reactor was charged with a solution of aqueous hydrobromic acid (47.6%, 125.0 kg, 5 equiv). Thiophene (12.5 kg, purity 99%, 1 equiv) was added to it at 25-30° C. Tetrabutylammonium bromide (0.625 kg, 0.13 equiv) was added to the reaction mass. The reaction mass was heated to 50-55° C. 50% Aqueous hydrogen peroxide solution (31.3 kg, 3.1 equiv) was added to the reaction mass over 10 h keeping the temperature in the range of 50-55° C. The reaction mass was then heated to 70-75° C. After reaction completion, the reaction mass was cooled to 20-25° C. and washed with 20% sodium metabisulphite solution (17 L), 2 N sodium hydroxide solution (62 L) and the crude product was subjected to fractional distillation using a 2 ft wire-mesh packed column to afford 2,3,5-tribromothiophene A. The spectral properties of this molecule are consistent with commercially available material.

ii. De-Bromination to Prepare Intermediate B:

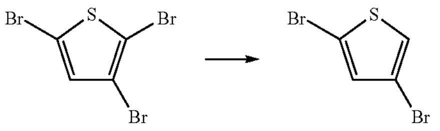

A B

Selective de-bromination of A provided 2,4 dibromothiophene B according to the following procedure. Dimethyl sulfoxide (DMSO, 330 L) was charged to reactor. 2,3,5-tribromothiophene A (33 kg, 1.0 equiv) was charged to the reaction mass under stirring. The reaction mass was cooled to 15-20° C. Sodium borohydride (7.8 kg, 2.0 equiv) was charged lot wise to the reaction mass in 2.0 h maintaining temperature 15 to 20° C. The reaction mass was heated to 20 to 25° C. and maintained until the reaction was completed. The reaction mass was quenched in water (660 L) at 10 to 15° C. and the product was extracted into toluene (5×165 L). The combined organic layer was washed with water (165 L). The organic layer was dried over anhydrous sodium sulfate (8.0 kg) and concentrated under reduced pressure below 50° C. to yield 2,4 dibromothiophene B. The spectral properties of this molecule are consistent with commercially available material.

iii. Alkynylation to Provide Intermediate II ($X^1$=Br):

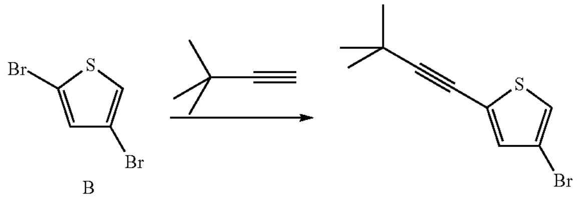

B

II ($X^1$ = Br)

The alkynylation of B to provide II (($X^1$=Br) was performed using the following procedure. 2,4-Dibromothiophene B (6 g, 24.8 mmol), $PdCl_2$ $(PPh_3)_2$ (522 mg, 0.74 mmol) and CuI (283 mg, 1.49 mmol) were added to a 250 mL round bottom flask and sealed with a rubber septum. The flask was degassed, then backfilled with argon in three repetitions, followed by addition of DMF (150 mL) and TEA (30 mL). 3,3-Dimethylbut-1-yne (2.87 mL, 23.56 mmol) was added. The reaction mixture was heated at 45° C. for two hours until the 2,4-dibromothiophene had been completely consumed. After filtering off the insoluble materials and removing the volatiles in vacuo, the residue was participated in EtOAc (150 mL) and water (100 mL plus 2 mL of ammonia). The organic phase was separated, washed with 5% LiCl aqueous solution and brine, dried over $Na_2SO_4$ and filtered. The filtrate was concentrated. The residue was purified by silica gel chromatography eluting with hexane to afford the title compound II ($X^1$=Br) as a faint yellow liquid.

MS (m/z): 243.1 $[M+H]^+$; $^1H$ NMR (400 MHz, $CDCl_3$) δ 7.02 (d, J=1.6 Hz, 1H), 6.95 (d, J=1.2 Hz, 1H), 1.25 (s, 9H).

Step 2: Synthesis of N-(5-(3,3-dimethylbut-1-ynyl)thiophen-3-yl)-1,4-dioxaspiro[4.5]decan-8-amine (IV) via N-arylation

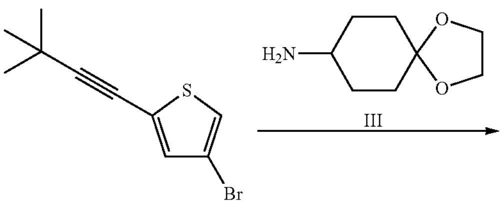

II ($X^1$ = Br)

-continued

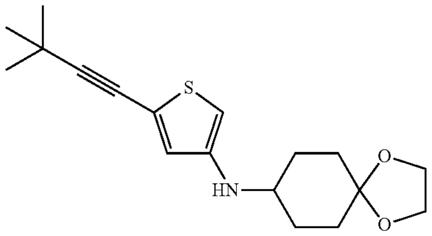

IV

The N-arylation reaction to provide IV was performed using the following procedure. A mixture of 4-bromo-2-(3,3-dimethylbut-1-ynyl)thiophene II ($X^1$═Br) (0.773 g, 3.18 mmol), CuI (30 mg, 0.160 mmol), cesium carbonate (2.072 g, 6.36 mmol), 2-acetylcyclohexanone (90 mg, 0.636 mmol) and 1,4-dioxa-spiro[4.5]dec-8-ylamine (1.0 g, 6.36 mmol) in DMF (1.6 mL) was degassed with $N_2$ then heated to 80° C. for 16 h in a sealed tube. The reaction was diluted with EtOAc, filtered through a Celite pad, washed with 5% LiCl aqueous solution, dried over sodium sulfate, filtered and concentrated. Flash chromatography (EtOAc:Hexanes) afforded the title compound IV.

MS (m/z): 320.2 $[M+H]^+$; $^1H$ NMR (400 MHz, $CDCl_3$) δ 6.52 (s, 1H), 5.76 (s, 1H), 3.93 (br. s, 5H), 3.20-3.10 (m, 1H), 2.09-1.95 (m, 2H), 1.80-1.39 (m, 6H), 1.28 (s, 9H).

Step 3: Synthesis of intermediate V ($X^2$═Cl)

B. Cyclization, Acylation, Diels-Alder and Saponification to Provide Intermediate 13:

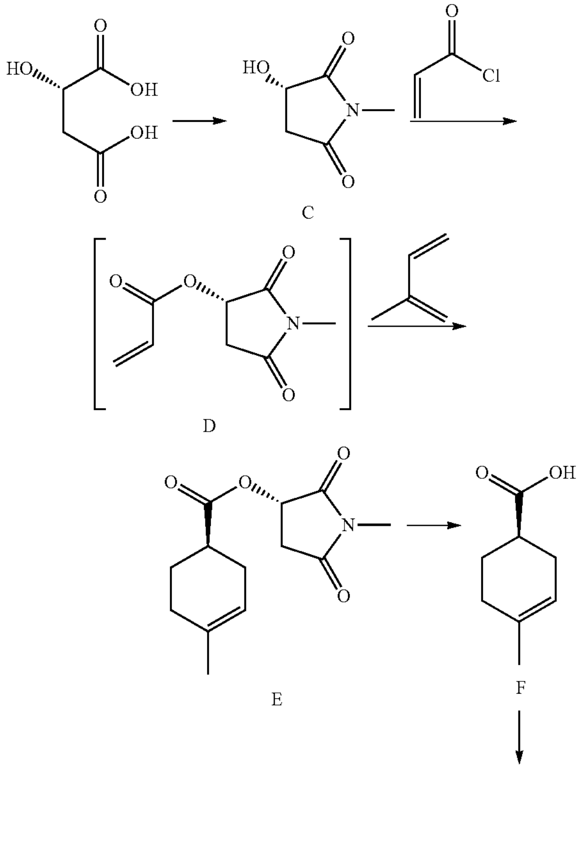

C

D

E

F

-continued

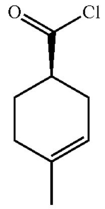

V (X2 = Cl)

i. Cyclization Reaction to Prepare Intermediate C:

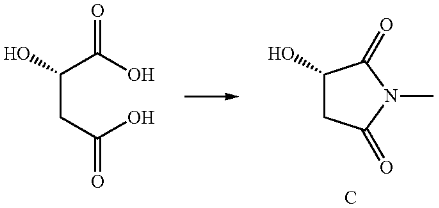

C

The cyclization of S-malic acid to provide C was performed using the following procedure. To a stirred solution of (S)-malic acid (10.0 kg, 1.0 equiv) in toluene (50 L) was added methyl amine (30 wt % in EtOH, 11.3 L, 1.22 equiv) in a 70 L reactor. The mixture was heated to reflux and the EtOH was removed by atmospheric distillation. The distillation was continued to azeoptropically remove the water formed in the reaction. The toluene distillate was separated from the water and returned to the reaction. Upon reaction completion as determined by GC, the mixture was cooled and concentrated under vacuum to a final volume of 14 L. Ethyl acetate (40 L) and silica gel (10 kg) were added to the reaction mixture and stirred at 60° C. for 18 h. The mixture was filtered and the solids were washed with 11 L of ethyl acetate. The combined organics were concentrated to 10 L and the resulting slurry was aged with agitation at 0° C. for 3 h. The mixture was filtered and the solids were washed with n-heptane (10 L). After drying the solids in an oven under vacuum, compound C was isolated (88% ee). Spectral data consistent with commercially available sample.

ii. Acylation and Diels-Alder to Prepare Intermediate 12:

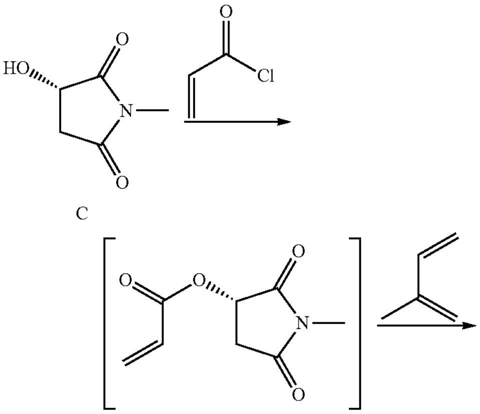

C

D

-continued

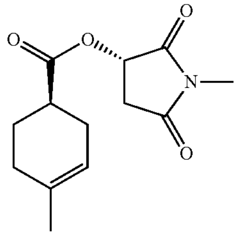

E

The acylation of C to provide D, and subsequent exposure thereof to isoprene under Diels-Alder afforded E using the following procedure. Charge dichloromethane (DCM, 38 L) and compound C (4.81 kg, 1 equiv) to a 70 L reactor and cool the slurry to −10 to −5° C. Charge triethylamine (5.28 kg 1.4 equiv) and once the mixture becomes homogeneous, charge acryloyl chloride (3.7 kg, 1.1 equiv) to the reactor at a rate to ensure that the reaction temperature does not exceed −5° C. Upon reaction completion as determined by GC, wash the reaction with 1 N HCl (20 kg) and allow the mixture to warm to ambient temperature. The organics are washed with 5% $NaHCO_3$ (24.3 kg) and 5% brine (23.8 kg). Dry the resulting organic phase with $Na_2SO_4$ (5.5 kg), filter the solids, and wash the filter cake with hexanes (8 L) to provide compound D in solution. Charge an appropriate amount of DCM (12 L) to this solution in order to achieve a final volume of 51 L. Split this mixture evenly between two reactors and cool the contents of the reactors to −10° C. Charge $TiCl_4$ (1 M in DCM, 4.4 kg, 0.24 equiv) to each reactor at a rate to ensure the temperature does not exceed −9° C. Charge isoprene (7.25 kg, 5.8 equiv) to the resulting slurry in each reactor. Stir the mixtures at −10° C. until the reaction is complete as determined by GC analysis. Charge solid $Na_2CO_3*10H_2O$ (2.26 kg) to each reaction mixture and warm the reactors' contents to 23° C. Stir for a NLT 2 h and filter the reaction mixtures in separate filters. Rinse the two filter cakes with DCM (2 L each) and wash the combined filtrate and rinses from each filtration with water (20 L each). Dry each organic mixture with $Na_2SO_4$ (2.6 kg each) and filter off the solids. Rinse the filter cakes with an appropriate amount of DCM. Separately concentrate both compound E containing DCM solutions to an oil. Return each concentrated oil to separate clean reactors and charge 7 volumes of methyl tert-butyl ether (MTBE, 30.8 L and 29.5 L, respectively) and heat the mixtures to 55° C. The following operations were performed separately for each solution: Charge 4 volumes of heptanes (17.6 L and 16.5 L, respectively) and allow mixture to return to 55° C. Ensure the solvent ratio is appropriate by $^1$H-NMR, if not then adjust. Filter the resulting fine slurry and gummy solids while at 55° C. and concentrate the resulting filtrate. Dissolve the resulting solids in 5 vol of isopropanol (IPA, 23 L and 20 L, respectively) at 45° C. and cool to −3 to 15° C. over 3 h and age slurry for 18 h. Filter the resulting slurry and rinse with a minimum volume of cold IPA. Dry the resulting solids in an oven at 40° C. under vacuum to provide compound E (96:4 dr). $^1$H NMR (400 MHz, $CDCl_3$) δ 5.46 (dd, J=8.7, 4.7 Hz, 1H), 5.36 (s, 1H), 3.16 (dd, J=18.3, 8.7 Hz, 1H), 3.05 (s, 3H), 2.64 (dd, J=18.3, 4.7 Hz, 1H), 2.54-2.64 (m, 1H), 2.24 (br. s, 2H), 2.02 (br. s, 3H), 1.69-1.82 (m, 1H), 1.65 (s, 3H).

iii. Saponification to Prepare Intermediate F:

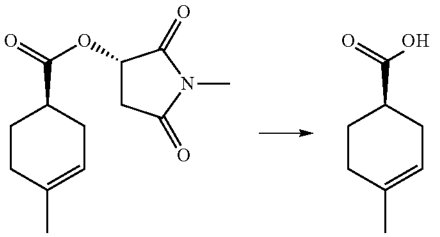

E F

The saponification of E to provide F was performed using the following procedure. Charge compound E (3.0 kg, 1.0 equiv) solution in tetrahydrofuran (THF, 34 L) to a 70 L reactor. Charge the reactor with water (27 L) and lithium hydroxide monohydrate (2.51 kg, 5 equiv) and stir the biphasic mixture at 20 to 27° C. until the reaction is complete as judged by GC. Concentrate the completed reaction to remove the THF and with stirring adjust the pH of the resulting aqueous mixture to 1-2 by adding 5 N HCl (40 L). Extract the acidic solution with a 98:2 mixture of hexanes:dichloromethane (25 L). Back extract the aqueous layer with 98:2 mixture of hexanes:dichloromethane (12.2 L) and dry the combined organics with sodium sulfate (1.7 kg). Filter off solids and rinse the filter cake with a 1:1 mixture of hexanes: dichloromethane (10 L). Concentrate the combined organics to dryness and continue drying the resulting solids in an oven at 40° C. under vacuum to afford compound F (90% ee). $^1$H NMR (400 MHz, $CDCl_3$) δ 5.46-5.31 (m, 1H), 2.48-2.60 (m, 1H), 2.15-2.33 (m, 2H), 2.11-1.92 (m, 3H), 1.82-1.62 (m, 1H), 1.66 (s, 3H)

Further to the above processes for obtaining compound F, in some embodiments, the enantiopurity of F can be increased by chiral resolution. Such methods are well known in the art.

iv. Conversion of Compound F to Intermediate V ($X^2$=Cl):

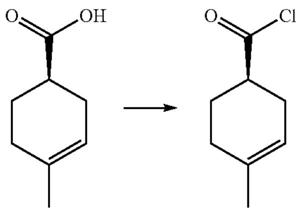

F V ($X^2$ = Cl)

The conversion of F to provide V ($X^2$=Cl) was performed using the following procedure. (1R)-4-Methyl-cyclohex-3-enecarboxylic acid F (209 mg, 1.5 mmol), azeotropically dried by evaporation from toluene, was treated with potassium phosphate tribasic (383 mg, 1.8 mmol), suspended in dichloromethane (4 mL) and treated with dimethylformamide (2 drops). The reaction mixture was cooled to 0° C. and treated dropwise with oxalyl chloride (0.3 mL, 3.2 mmol). The reaction mixture was allowed to warm to ambient temperature while stirring for 2 h. After filtering the solids, the solution was concentrated, treated with hexanes and concentrated again to afford (R) 4-methyl-cyclohex-3-enecarbonyl chloride V as a light yellow oil which was used immediately in the next step.

Step 4: Synthesis of (R)—N-(5-(3,3-dimethylbut-1-yn-1-yl)thiophen-3-yl)-4-methyl-N-(1,4-dioxaspiro[4.5]decan-8-yl)cyclohex-3-enecarboxamide (VI) via acylation

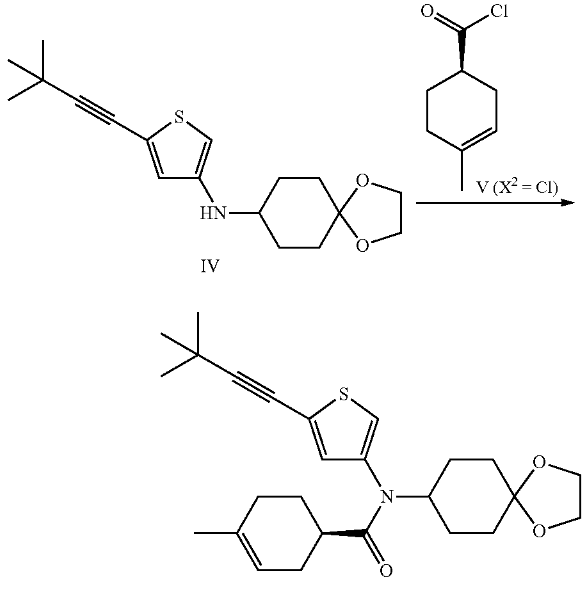

IV

VI

Acylation of IV to provide VI was performed using the following procedure. N-(5-(3,3-dimethylbut-1-ynyl)thiophen-3-yl)-1,4-dioxaspiro[4.5]decan-8-amine IV (10 g, 31.3 mmol) and diisopropyl ethylamine (DIEA) (8.1 g, 11.2 mL, 62.6 mmol, 2.0 equiv) were dissolved in DCE (100 mL) in a 500 mL round-bottomed flask. The solution was cooled to 0° C. in an ice-water bath. Acyl chloride V (5.9 g, 37.6 mmol, 1.2 equiv) in DCE (50 mL) was added dropwise via a syringe. After the addition, HPLC showed 50% conversion. The reaction was stirred for 15 min at 0° C. and another 10 min at room temperature. The reaction was diluted with DCM (200 mL), and the organics were washed with saturated $NH_4Cl$ (2×100 mL). After drying over $Na_2SO_4$, the organic layer was concentrated to give a yellow foamy solid VI. This compound was taken to the next step without further purification.

MS (m/z): 442.2 $[M+H]^+$; $^1$H NMR (400 MHz, $CDCl_3$) δ 6.86 (d, J=1.6 Hz, 1H), 6.79 (d, J=1.2 Hz, 1H), 5.28 (m, 1H), 4.57 (dd, J=16.6, 7.7 Hz, 1H), 3.93-3.76 (m, 4H), 2.72 (m, 1H), 2.23 (m, 2H), 2.00 (m, 2H), 1.95-1.67 (m, 10H), 1.56 (s, 3H), 1.25 (s, 9H).

Step 5: Synthesis of (R)—N-(5-(3,3-dimethylbut-1-yn-1-yl)thiophen-3-yl)-4-methyl-N-(4-oxocyclohexyl)cyclohex-3-enecarboxamide (VII) via hydrolysis of ketal

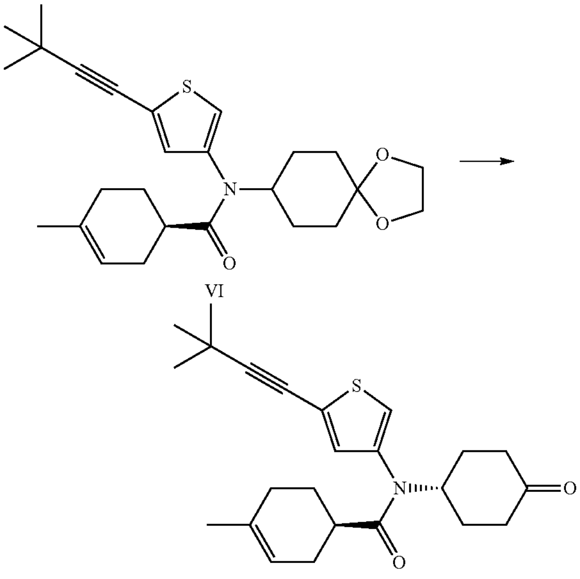
VI

VII

Hydrolysis of VI to provide VII was performed using the following procedure. The ketal VI (15.6 g crude from 3995-161) was dissolved in THF (200 mL) and 4 N HCl (100 mL) in a 1.0 L round-bottomed flask. The solution was heated at 45° C. for 90 min. After cooling to room temperature, THF was removed in vacuo. The resulting solution was poured into EtOAc (400 mL) and $H_2O$ (200 mL). The aqueous layer was extracted with EtOAc (200 mL). The combined EtOAc was then washed with saturated $NaHCO_3$ (200 mL), $H_2O$ (200 mL) and brine (200 mL). After drying over $Na_2SO_4$, the organic layer was concentrated to give a yellow foamy solid VII. This compound was taken to the next step without further purification.

MS (m/z): 398.2 $[M+H]^+$; $^1$H NMR (400 MHz, $CDCl_3$) δ 6.87 (d, J=1.6 Hz, 1H), 6.80 (d, J=1.2 Hz, 1H), 5.30 (m, 1H), 5.02 (m, 1H), 2.52 (m, 1H), 2.35 (m, 1H), 2.24 (m, 1H), 2.08 (m, 2H), 1.97-1.63 (m, 10H), 1.58 (s, 3H), 1.29 (s, 9H).

Step 6: Synthesis of (R)—N-(5-(3,3-dimethylbut-1-yn-1-yl)thiophen-3-yl)-4-methyl-N-((3S,6S)-1-oxaspiro[2.5]octan-6-yl)cyclohex-3-enecarboxamide (VIII)

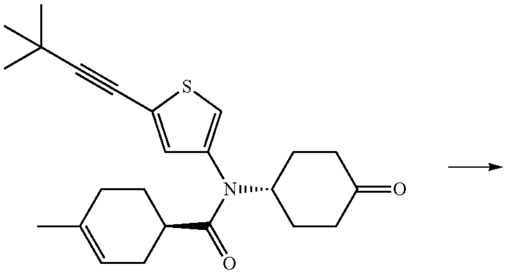
VII

-continued

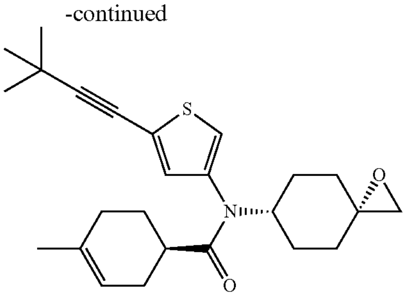

VIII

Conversion of VII to provide VIII was performed using the following procedure. Trimethylsulfoxonium chloride (4.96 g, 38.8 mmol, 1.25 equiv) was dissolved in DMSO (100 mL) in a 500 mL round-bottomed flask. The flask was cooled in an ice-water bath and NaH (1.4 g, 34.1 mmol, 1.1 equiv) was added portion-wise. The ice-water bath was removed and the solution was stirred at room temperature for 1 h. A solution of the ketone VII (12 g crude, 31 mmol) in THF (100 mL) was added to the flask via a syringe over 15 min. After addition, the reaction was stirred at room temperature for 30 min and HPLC showed the reaction was complete. The reaction was quenched by slow addition of 10% citric acid. The mixture was then poured into EtOAc (1.0 L) and $H_2O$ (250 mL) in a 2.0 L reparatory funnel. After separation, EtOAc layer was washed with $H_2O$ (2×200 mL), 5% LiCl (2×100 mL), and brine (200 mL). After drying over $Na_2SO_4$, the organic layer was concentrated to give a yellow foamy solid VIII (14 g). This crude residue was purified by silica gel column chromatography (220 g, 0 to 40% EtOAc in hexanes) to give a yellow foamy solid.

MS (m/z): 412.2 $[M+H]^+$; $^1H$ NMR (400 MHz, $CDCl_3$) δ 6.86 (d, J=1.6 Hz, 1H), 6.81 (d, J=1.2 Hz, 1H), 5.29 (s, 1H), 4.79-4.59 (m, 1H), 2.60 (s, 2H), 2.35-2.20 (m, 2H), 2.10-2.03 (m, 2H), 1.91-1.71 (m, 8H), 1.58 (s, 3H), 1.50-1.43 (m, 2H), 1.31 (s, 9H), 1.30-1.24 (m, 1H).

Step 7: Synthesis of 5-(3,3-dimethylbut-1-yn-1-yl)-3-(R)-4-methyl-N-((3S,6S)-1-oxaspiro[2.5]octan-6-yl)cyclohex-3-enecarboxamido)thiophene-2-carboxylic acid (X) via carboxylation

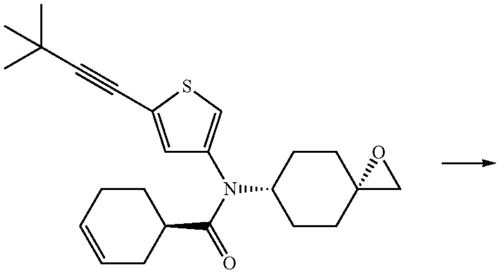

VIII

-continued

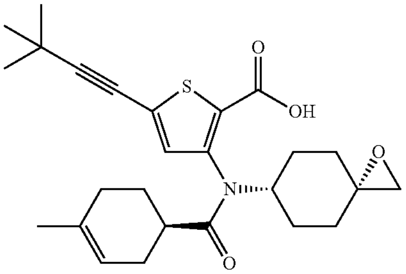

X

Carboxylation of VIII to provide X was performed using the following procedure. The epoxide VIII (6.17 g, 15 mmol, 1.0 equiv) was dissolved in THF (70 mL) in a 250 mL two-necked round-bottomed flask. The solution was cooled to −78° C. in an acetone-dry ice bath. To this solution, LDA (22.5 mL, 45 mmol, 3.0 equiv) was added dropwise via a syringe while maintained internal temperature lower than −70° C. After addition, the solution was stirred at −78° C. for 2 h. $CO_2$ was bubbled into solution for 10 min (dark brown solution changed to orange, internal temperature rose from −70° C. to −40° C.). Isopropanol (10 mL) was added to the solution, followed by 10% citric acid (100 mL). The mixture was poured into EtOAc (500 mL) and organics were washed with 10% citric acid (2×100 mL) and brine (100 mL). After drying over $Na_2SO_4$ and concentration to dryness in vacuo, the residue was purified by silica gel chromatography (120 g silica, 0 to 100% DCM in EtOAc) to give a yellow solid X.

MS (m/z): 456.2 $[M+H]^+$; $^1H$ NMR (400 MHz, dmso) δ 13.50 (br, 1H), 7.27, 7.23 (s, 1H, atropisomers), 5.25 (d, J=14.9 Hz, 1H), 4.48 (t, J=11.5 Hz, 1H), 2.59-2.53 (m, 1H), 2.15-1.78 (m, 4H), 1.68 (m, 4H), 1.62 (m, 5H), 1.51 (s, 3H), 1.46-1.32 (m, 1H), 1.28 (s, 9H), 1.23-0.96 (m, 2H).

Step 8: Synthesis of 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid (I)

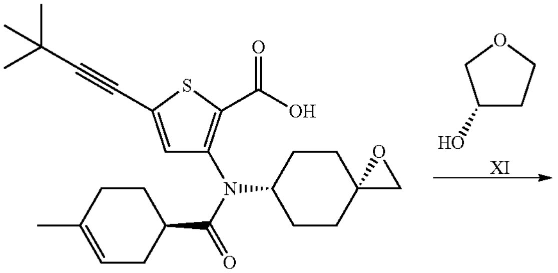

X

-continued

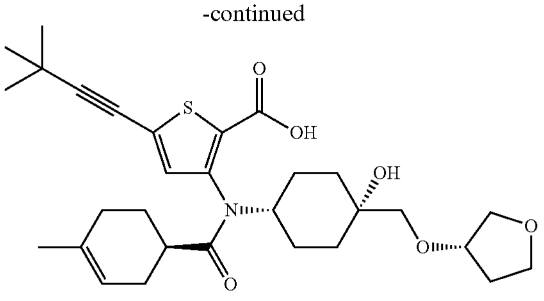

I

Conversion of X to provide I was performed using the following procedure. (S)-3-Hydroxytetrahydrofuran XI (6.3 g, 5.7 mL, 71 mmol, 5.0 equiv) was dissolved in NMP (30 mL) in a 200 mL round-bottomed flask. At room temperature, KOtBu (6.4 g, 57 mmol, 4.0 equiv) was added portionwise over 5 min. The resulting solution was stirred at room temperature for 20 min. The acid X (6.5 g, 14.28 mmol, 1.0 equiv) was then added in one portion as solid and the rest was rinsed into flask with 10 mL NMP. The reaction was stirred at 35° C. for 16 h. After cooling to 0° C. in an ice-water bath, the pH of the mixture was adjusted to 3 by adding 4 N HCl dropwise. The mixture was then poured into EtOAc (500 mL) and organics were washed with 5% LiCl (4×50 mL) and brine (50 mL). After drying over $Na_2SO_4$ and concentrated to dryness in vacuo, the residue was purified by silica gel chromatography (120 g silica, 0 to 100% DCM in EtOAc) to give a yellow solid I.

MS (m/z): 544.2 $[M+H]^+$; $^1H$ NMR (400 MHz, dmso) δ 13.47 (s, 1H), 7.20, 7.16 (s, 1H, atropisomers), 5.24 (d, J=14.2 Hz, 1H), 4.30 (s, 1H), 4.08-3.95 (m, 2H), 3.74-3.56 (m, 4H), 3.12-2.96 (m, 2H), 2.13-2.01 (m, 1H), 1.97-1.71 (m, 5H), 1.71-1.59 (m, 2H), 1.59-1.31 (m, 11H), 1.31-1.01 (m, 10H).

We claim:

1. A compound of Formula VI:

(VI)

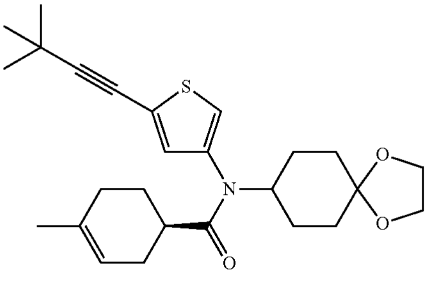

named (R)—N-(5-(3,3-dimethylbut-1-yn-1-yl)thiophen-3-yl)-4-methyl-N-(1,4-dioxaspiro[4.5]decan-8-yl)cyclohex-3-enecarboxamide, or a stereoisomer, mixture of stereoisomers, or salt thereof.

2. A compound of Formula VII:

(VII)

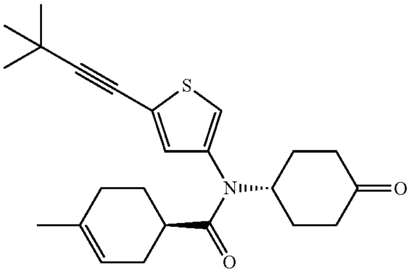

or a stereoisomer, mixture of stereoisomers, or salt thereof.

3. A compound of Formula VIII:

(VIII)

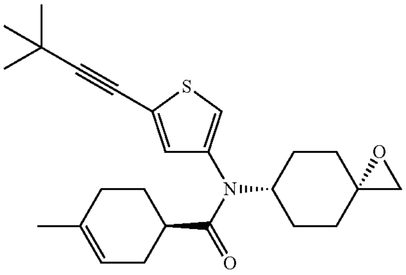

named (R)—N-(5-(3,3-dimethylbut-1-yn-1-yl)thiophen-3-yl)-4-methyl-N-(4-oxocyclohexyl)cyclohex-3-enecarboxamide, or a stereoisomer, mixture of stereoisomers, or salt thereof.

4. A compound of Formula IX:

(IX)

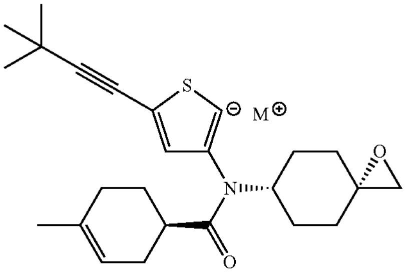

named 5-(3,3-dimethylbutyn-1-yl)-3-[(cis-4-hydroxy-4-{[(3S)-tetrahydrofuran-3-yloxy]methyl cyclohexyl)[(1R)-4-methylcyclohex-3-en-1-yl]carbonyl}amino] thiophene metal salt, or a stereoisomer or a mixture of stereoisomers thereof, wherein M is a metal.

5. The compound of claim 4, wherein M is lithium.

* * * * *